(12) United States Patent
Di et al.

(10) Patent No.: US 8,753,642 B2
(45) Date of Patent: Jun. 17, 2014

(54) METHOD OF TREATING HEPATITIS C VIRUS

(75) Inventors: Rong Di, East Brunswick, NJ (US); Nilgun E. Tumer, Belle Mead, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1205 days.

(21) Appl. No.: 12/449,076

(22) PCT Filed: Jan. 18, 2008

(86) PCT No.: PCT/US2008/000684
§ 371 (c)(1),
(2), (4) Date: Jan. 12, 2010

(87) PCT Pub. No.: WO2008/088875
PCT Pub. Date: Jul. 24, 2008

(65) Prior Publication Data
US 2010/0120680 A1 May 13, 2010

Related U.S. Application Data

(60) Provisional application No. 60/881,365, filed on Jan. 19, 2007.

(51) Int. Cl.
*C07K 14/00* (2006.01)

(52) U.S. Cl.
USPC .................. 424/184.1; 530/350; 424/185.1; 424/192.1

(58) Field of Classification Search
None
See application file for complete search history.

(56) References Cited

U.S. PATENT DOCUMENTS

| 5,985,655 A | 11/1999 | Anderson et al. |
| 6,069,133 A | 5/2000 | Chiou et al. |
| 6,627,736 B1 | 9/2003 | Tumer |
| 2004/0241673 A1 | 12/2004 | Tumer et al. |

OTHER PUBLICATIONS

Rutgers online publication via http://nih.rutgers.edu/2006_01_01 archive.html. NIH grants awarded to Rutgers Faculty. "Effect of Pokeweed antiviral protein on hepatitis C virus IRES", PI: DI, Rong, Jan. 15, 2006.*

Rollier et al. Control of Heterologous Hepatitis C Virus Infection in Chimpanzees is Associated with the Quality of Vaccine-Induced Peripheral T-Helper Immune Response. J Virol. 2004, 78(1): 187-196.*

Shirai et al. An Epitope in Hepatitis C Virus Core Region Recognized by Cytotoxic T Cells in Mice and Humans. J Virol, 1994, 68(5): 3334-3342.*

Huang et al. Recent development o therapeutics for chronic HCV infection. Antiviral Res 71 (2006) 351-362.*

Tan et al. Strategies for hepatitis C therapeutic intervention: now and next. Curr Opin in Pharmacology, 2004, 4: 465-470.*

Racanelli et al. Presentation of HCV antigens to naive CD8+T cells: why the where, when, what and how are important for virus control and infection outcome. Clin Immunol. Jul. 2007;124(1):5-12.*

(Continued)

*Primary Examiner* — Michelle S Horning
(74) *Attorney, Agent, or Firm* — Dann, Dorfman, Herrell & Skillman; Kathleen D. Rigaut

(57) ABSTRACT

A method of treating or inhibiting hepatitic C virus (HCV). The method comprises administering an effective amount of at least one pokeweed antiviral protein (PAP) mutant alone or in combination with other anti-HCV agents.

10 Claims, 8 Drawing Sheets

(56) References Cited

OTHER PUBLICATIONS

Koziel et al. Hepatitis C virus (HCV)-specific cytotoxic T lymphocytes recognize epitopes in the core and envelope proteins of HCV. J Virol. Dec. 1993;67(12):7522-32.*

Berzofsky et al. Progress on new vaccine strategies against chronic viral infections. J Clin Invest. Aug. 2004;114(4):450-62.*

Baker et al. Protein Structure Prediction and Structural Genomics. Science. 294, 92 (2001). p. 93-96.*

Attwood. The Babel of Bioinformatics. Science (2000): vol. 290, No. 5491. p. 471-473.*

He, Y-W, et al., "Inhibition of Hepatitis Virus Replication by Pokeweed Antiviral Protein In Vitro," World J. Gasteroenterology, Mar. 14, 2008, vol. 14, No. 10, pp. 1592-1597. Database CAPLUS on STN, AN 2007:1460215. Chen, R., et al. "Influence on Hepatitis C Virus Replication in an Infection Cell Model," Jan. 2006, vol. 16. No. 4, pp. 226-228.

Hogg, A., et al. Sugar-mediated Latticeontacts in Cystals of a Plant Glycoprotein, Acta. Cryst. Oct. 2002, vol. D58, No. 10-1, pp. 1734-1739.

Hudack, K.A., et al., A C-terminal Deletion Mutant of Pokeweed Antiviral Protein Inhibits Programmed +1 Ribosomal Frameshifting and Ty 1 Retrotransposition without Depurinating the Sarcin/Ricin Loop of rRNA . Virology, Sep. 2001, vol. 279, pp. 292-301.

Saito, et al., Proc. Natl. Acad. Sci. USA 87:6547-6549 (1990).
Hoofnagle, Adv. Intern. Med. 39:241-275 (1994).
Wang and Heinz, Prog. Drug Res. (Spec. No): 79-110 (2001).
Choo, et al., Science 244:359-362 (1989).
Hijikata, et al., Proc. Natl. Acad. Sci. USA 88:5547-5551 (1991).
Grakoui et al., J. Virol. 67:1385-1395 (1993).
Bartenschlager, et al., J. Virol. 68:5054-5055 (1994).
Wang, et al., J. Virol. 67:3338-3344 (1993).
Brown, et al., Nucleic Acids Res. 20:5041-5045 (1992).
Honda, et al., RNA 2:955-968 (1996).
Wang, et al., RNA 1:526-537 (1995).
Kieft, et al., RNA 7:194-206 (2001).
Klinck, et al, RNA 6:1423-1431 (2000).
Lukavsky, et al., Nat. Struct. Biol. 7:1105-1110 (2000).
Correll et al., Proc. Natl. Acad. Sci. 95:13436-13441 (1998).
Seggerson and Moore, RNA 4:1203-1215 (1998).
Leontis and Westhof, J. Mol. Biol. 283:571-583 (1998).
Rijnbrand, et al., Virology 226:47-56 (1996).
Irvin, et al., Pharmac. Ther. 55:279-302 (1992).
Dore, et al., Nuc. Acids Res. 21(18):4200-05 (1993).
Monzingo, et al., J. Mol. Biol. 233:705-15 (1993).
Turner. et al., Proc. Natl. Acad. Sci. USA 92:8448-52 (1995).
Chen, et. al., Human Gene Therapy 5:429-435 (1994).
Ferkol, et al., FASEB 7:1081-1091 (1993).
Perales, et al., PNAS 91:4086-4090 (1994).
Midoux, et al., Nucleic Acids Research 21(4):871-878 (1993).
Martinez-Fong, Hepatology 20(6):1602-1608 (1994).
Plank, et al., Bioconjugate Chem. 3:533-539 (1992).
Grandis, et al., J. Bacteriology 169:4313-4319 (1987).
Jackson, et al., FEMS Microbiology Letters 44:109-114 (1987).
Lamb, et al., Eur. J. Biochem, 148:265-270 (1985).
Iizuka, et al., Methods 11:353-60 (1997).

* cited by examiner

FIGURE 3

| Construct | Mutation | Cytotoxicity | Depurination (% of wild type) | Translation (% vector control) | mRNA destabilization |
|---|---|---|---|---|---|
| NT501 | N70A | No | Yes (96) | 71.7 | Yes |
| NT538 | L71R | No | Yes (105) | 33.2 | No |
| NT255 | G75D | No | No (0) | 100 | No |
| NT532 | V73E | No | Yes (90) | 73.1 | Yes |
| NT242 | Y123A | No | Yes (61) | 88.8 | No |
| NT224 | E176V | No | No (0) | 75.2 | No |
| NT188 | Wild type | Yes | Yes (100) | 30.3 | Yes |
| NT616 | Vector | No | No (0) | 100 | No |

SEQUENCE LISTING

```
<160> NUMBER OF SEQ ID NOS: 43

<210> SEQ ID NO 1
<211> LENGTH: 383
<212> TYPE: RNA
<213> ORGANISM: Hepatitis C virus

<400> SEQUENCE: 1
gccagccccc gauuggggc  gacacuccac  cauagaucac  uccccuguga  ggaacuacug     60
ucuucacgca  gaaagcgucu  agccauggcg  uuaguaugag  ugucgugcag  ccuccaggac    120
cccccucccc  gggagagcca  uaguggucug  cggaaccggu  gaguacaccg  gaauugccag    180
```

-continued

```
gacgaccggg uccuuucuug gaucaacccg cucaaugccu ggagauuugg gcgugccccc    240
gcgagacugc uagccgagua guguugdguc gcgaaaggcc uugugguacu gccugauagg    300
gugcuugcga gugccccggg aggucucgua gaccgugcac caugagcacg aauccuaaac    360
cucaaagaaa aaccaaacgu aac                                            383
```

<210> SEQ ID NO 2
<211> LENGTH: 4
<212> TYPE: PRT
<213> ORGANISM: Phytolacca americana

<400> SEQUENCE: 2

Pro Asp Val Ala
 1

<210> SEQ ID NO 3
<211> LENGTH: 5
<212> TYPE: PRT
<213> ORGANISM: Phytolacca americana

<400> SEQUENCE: 3

Pro Asp Val Ala Leu
 1               5

<210> SEQ ID NO 4
<211> LENGTH: 6
<212> TYPE: PRT
<213> ORGANISM: Phytolacca americana

<400> SEQUENCE: 4

Pro Asp Val Ala Leu Leu
 1               5

<210> SEQ ID NO 5
<211> LENGTH: 7
<212> TYPE: PRT
<213> ORGANISM: Phytolacca americana

<400> SEQUENCE: 5

Pro Asp Val Ala Leu Leu Asn
 1               5

<210> SEQ ID NO 6
<211> LENGTH: 15
<212> TYPE: PRT
<213> ORGANISM: Phytolacca americana

<400> SEQUENCE: 6

Pro Asp Val Ala Leu Leu Asn Tyr Val Gly Gly Ser Cys Gln Thr
 1               5                  10                  15

<210> SEQ ID NO 7
<211> LENGTH: 16
<212> TYPE: PRT
<213> ORGANISM: Phytolacca americana

<400> SEQUENCE: 7

Pro Asp Val Ala Leu Leu Asn Tyr Val Gly Gly Ser Cys Gln Thr Thr
 1               5                  10                  15

<210> SEQ ID NO 8
<211> LENGTH: 16
<212> TYPE: PRT
<213> ORGANISM: Phytolacca americana -continued

<400> SEQUENCE: 8

Met Leu Arg Arg Asn Asn Leu Tyr Glu Met Gly Tyr Ser Asp Pro Phe
1               5                   10                  15

<210> SEQ ID NO 9
<211> LENGTH: 16
<212> TYPE: PRT
<213> ORGANISM: Phytolacca americana

<400> SEQUENCE: 9

Met Leu Arg Arg Asn Asn Leu Tyr Val Met Asp Tyr Ser Asp Pro Phe
1               5                   10                  15

<210> SEQ ID NO 10
<211> LENGTH: 16
<212> TYPE: PRT
<213> ORGANISM: Phytolacca americana

<400> SEQUENCE: 10

Pro Asp Val Ala Leu Leu Asn Tyr Val Gly Gly Ser Ala Gln Thr Thr
1               5                   10                  15

<210> SEQ ID NO 11
<211> LENGTH: 16
<212> TYPE: PRT
<213> ORGANISM: Phytolacca americana

<400> SEQUENCE: 11

Pro Asp Val Ala Leu Lys Asn Tyr Val Gly Gly Ser Cys Gln Thr Thr
1               5                   10                  15

<210> SEQ ID NO 12
<211> LENGTH: 16
<212> TYPE: PRT
<213> ORGANISM: Phytolacca americana

<400> SEQUENCE: 12

Pro Asp Val Ala Leu Leu Ala Tyr Val Gly Gly Ser Cys Gln Thr Thr
1               5                   10                  15

<210> SEQ ID NO 13
<211> LENGTH: 16
<212> TYPE: PRT
<213> ORGANISM: Phytolacca americana

<400> SEQUENCE: 13

Pro Asp Val Ala Leu Leu Arg Tyr Val Gly Gly Ser Cys Gln Thr Thr
1               5                   10                  15

<210> SEQ ID NO 14
<211> LENGTH: 16
<212> TYPE: PRT
<213> ORGANISM: Phytolacca americana

<400> SEQUENCE: 14

Pro Asp Val Ala Leu Lys Ala Tyr Val Gly Gly Ser Cys Gln Thr Thr
1               5                   10                  15

<210> SEQ ID NO 15
<211> LENGTH: 7
<212> TYPE: PRT
<213> ORGANISM: Phytolacca americana

<400> SEQUENCE: 15

```
<210> SEQ ID NO 16
<211> LENGTH: 7
<212> TYPE: PRT
<213> ORGANISM: Phytolacca americana

<400> SEQUENCE: 16

Pro Asp Val Ala Leu Leu Ala
 1               5

<210> SEQ ID NO 17
<211> LENGTH: 7
<212> TYPE: PRT
<213> ORGANISM: Phytolacca americana

<400> SEQUENCE: 17

Pro Asp Val Ala Leu Leu Arg
 1               5

<210> SEQ ID NO 18
<211> LENGTH: 7
<212> TYPE: PRT
<213> ORGANISM: Phytolacca americana

<400> SEQUENCE: 18

Pro Asp Val Ala Leu Leu Asp
 1               5

<210> SEQ ID NO 19
<211> LENGTH: 942
<212> TYPE: DNA
<213> ORGANISM: Phytolacca americana
<220> FEATURE:
<221> NAME/KEY: CDS
<222> LOCATION: (1)..(939)

<400> SEQUENCE: 19 atg aag tcg atg ctt gtg gtg aca ata tca ata tgg ctc att ctt gca      48
Met Lys Ser Met Leu Val Val Thr Ile Ser Ile Trp Leu Ile Leu Ala
 1               5                  10                  15 cca act tca act tgg gct gtg aat aca atc atc tac aat gtt gga agt      96
Pro Thr Ser Thr Trp Ala Val Asn Thr Ile Ile Tyr Asn Val Gly Ser
             20                  25                  30 acc acc att agc aaa tac gcc act ttt ctg aat gat ctt cgt aat gaa     144
Thr Thr Ile Ser Lys Tyr Ala Thr Phe Leu Asn Asp Leu Arg Asn Glu
         35                  40                  45 gcg aaa gat cca agt tta aaa tgc tat gga ata cca atg ctg ccc aat     192
Ala Lys Asp Pro Ser Leu Lys Cys Tyr Gly Ile Pro Met Leu Pro Asn
     50                  55                  60 aca aat aca aat cca aag tac gtg ttg gtt gag ctc caa ggt tca aat     240
Thr Asn Thr Asn Pro Lys Tyr Val Leu Val Glu Leu Gln Gly Ser Asn
 65                  70                  75                  80 aaa aaa acc atc aca cta atg ctg aga cga aac aat ttg tat gtg atg     288
Lys Lys Thr Ile Thr Leu Met Leu Arg Arg Asn Asn Leu Tyr Val Met
                 85                  90                  95 ggt tat tct gat ccc ttt gaa acc aat aaa tgt cgt tac cat atc ttt     336
Gly Tyr Ser Asp Pro Phe Glu Thr Asn Lys Cys Arg Tyr His Ile Phe
            100                 105                 110 aat gat atc tca ggt act gaa cgc caa gat gta gag act act ctt tgc     384
Asn Asp Ile Ser Gly Thr Glu Arg Gln Asp Val Glu Thr Thr Leu Cys
        115                 120                 125 cca aat gcc aat tct cgt gtt act aaa aac ata aac ttt gat agt cga     432
```

```
Pro Asn Ala Asn Ser Arg Val Thr Lys Asn Ile Asn Phe Asp Ser Arg
        130                 135                 140 tat cca aca ttg gaa tca aaa gcg gga gta aaa tca aga agt cag gtc      480
Tyr Pro Thr Leu Glu Ser Lys Ala Gly Val Lys Ser Arg Ser Gln Val
145                 150                 155                 160 caa ctg gga att caa ata ctc gac agt aat att gga aag att tct gga      528
Gln Leu Gly Ile Gln Ile Leu Asp Ser Asn Ile Gly Lys Ile Ser Gly
                165                 170                 175 gtg atg tca ttc act gag aaa acc gaa gcc gaa ttc cta ttg gta gcc      576
Val Met Ser Phe Thr Glu Lys Thr Glu Ala Glu Phe Leu Leu Val Ala
            180                 185                 190 ata caa atg gta tca gag gca gca aga ttc aag tac ata gag aat cag      624
Ile Gln Met Val Ser Glu Ala Ala Arg Phe Lys Tyr Ile Glu Asn Gln
        195                 200                 205 gtg aaa act aat ttt aac aga gca ttc aac cct aat ccc aaa gta ctt      672
Val Lys Thr Asn Phe Asn Arg Ala Phe Asn Pro Asn Pro Lys Val Leu
    210                 215                 220 aat ttg caa gag aga tgg ggt aag att tca aca gca att cat gat gcc      720
Asn Leu Gln Glu Arg Trp Gly Lys Ile Ser Thr Ala Ile His Asp Ala
225                 230                 235                 240 aag aat gga gtt tta ccc aaa cct ctc gag cta gtg gat gcc agt ggt      768
Lys Asn Gly Val Leu Pro Lys Pro Leu Glu Leu Val Asp Ala Ser Gly
                245                 250                 255 gcc aag tgg ata gtg ttg aga gtg gat gaa atc aag cct gat gta gca      816
Ala Lys Trp Ile Val Leu Arg Val Asp Glu Ile Lys Pro Asp Val Ala
            260                 265                 270 ctc tta aac tac gtt ggt ggg agc tgt cag aca act tat aac caa aat      864
Leu Leu Asn Tyr Val Gly Gly Ser Cys Gln Thr Thr Tyr Asn Gln Asn
        275                 280                 285 gcc atg ttt cct caa ctt ata atg tct act tat tat aat tac atg gtt      912
Ala Met Phe Pro Gln Leu Ile Met Ser Thr Tyr Tyr Asn Tyr Met Val
    290                 295                 300 aat ctt ggt gat cta ttt gaa gga ttc tga                              942
Asn Leu Gly Asp Leu Phe Glu Gly Phe
305                 310

<210> SEQ ID NO 20
<211> LENGTH: 313
<212> TYPE: PRT
<213> ORGANISM: Phytolacca americana

<400> SEQUENCE: 20

Met Lys Ser Met Leu Val Val Thr Ile Ser Ile Trp Leu Ile Leu Ala
1               5                   10                  15

Pro Thr Ser Thr Trp Ala Val Asn Thr Ile Ile Tyr Asn Val Gly Ser
                20                  25                  30

Thr Thr Ile Ser Lys Tyr Ala Thr Phe Leu Asn Asp Leu Arg Asn Glu
            35                  40                  45

Ala Lys Asp Pro Ser Leu Lys Cys Tyr Gly Ile Pro Met Leu Pro Asn
        50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
                100                 105                 110

Asn Asp Ile Ser Gly Thr Glu Arg Gln Asp Val Glu Thr Thr Leu Cys
            115                 120                 125

Pro Asn Ala Asn Ser Arg Val Thr Lys Asn Ile Asn Phe Asp Ser Arg
```

```
                130                 135                 140
Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
                180                 185                 190

Ile Gln Met Val Ser Glu Ala Ala Arg Phe Lys Tyr Ile Glu Asn Gln
                195                 200                 205

Val Lys Thr Asn Phe Asn Arg Ala Phe Asn Pro Asn Pro Lys Val Leu
                210                 215                 220

Asn Leu Gln Glu Arg Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
                260                 265                 270

Leu Leu Asn Tyr Val Gly Gly Ser Cys Gln Thr Thr Tyr Asn Gln Asn
                275                 280                 285

Ala Met Phe Pro Gln Leu Ile Met Ser Thr Tyr Tyr Asn Tyr Met Val
                290                 295                 300

Asn Leu Gly Asp Leu Phe Glu Gly Phe
305                 310

<210> SEQ ID NO 21
<211> LENGTH: 1379
<212> TYPE: DNA
<213> ORGANISM: Phytolacca americana
<220> FEATURE:
<221> NAME/KEY: CDS
<222> LOCATION: (225)..(1163)

<400> SEQUENCE: 21
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa  gttgtgagtt     180 aactacaggg cgaaagtatt ggaactagct agtaggaagg gaag atg aag tcg atg     236
                                                 Met Lys Ser Met
                                                  1 ctt gtg gtg aca ata tca ata tgg ctc att ctt gca cca act tca act     284
Leu Val Val Thr Ile Ser Ile Trp Leu Ile Leu Ala Pro Thr Ser Thr
 5                  10                  15                  20 tgg gct gtg aat aca atc atc tac aat gtt gga agt acc acc att agc     332
Trp Ala Val Asn Thr Ile Ile Tyr Asn Val Gly Ser Thr Thr Ile Ser
                 25                  30                  35 aaa tac gcc act ttt ctg aat gat ctt cgt aat gaa gcg aaa gat cca     380
Lys Tyr Ala Thr Phe Leu Asn Asp Leu Arg Asn Glu Ala Lys Asp Pro
             40                  45                  50 agt tta aaa tgc tat gga ata cca atg ctg ccc aat aca aat aca aat     428
Ser Leu Lys Cys Tyr Gly Ile Pro Met Leu Pro Asn Thr Asn Thr Asn
         55                  60                  65 cca aag tac gtg ttg gtt gag ctc caa ggt tca aat aaa aaa acc atc     476
Pro Lys Tyr Val Leu Val Glu Leu Gln Gly Ser Asn Lys Lys Thr Ile
     70                  75                  80 aca cta atg ctg aga cga aac aat ttg tat gtg atg ggt tat tct gat     524
Thr Leu Met Leu Arg Arg Asn Asn Leu Tyr Val Met Gly Tyr Ser Asp
 85                  90                  95                 100
```

```
ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
            105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
        120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
            135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
        150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
            230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta gcc tac     1052
Val Leu Arg Val Asp Glu Ile Lys Pro Asp Val Ala Leu Leu Ala Tyr
                265                 270                 275 gtt ggt ggg agc tgt cag aca act tat aac caa aat gcc atg ttt cct     1100
Val Gly Gly Ser Cys Gln Thr Thr Tyr Asn Gln Asn Ala Met Phe Pro
            280                 285                 290 caa ctt ata atg tct act tat tat aat tac atg gtt aat ctt ggt gat     1148
Gln Leu Ile Met Ser Thr Tyr Tyr Asn Tyr Met Val Asn Leu Gly Asp
        295                 300                 305 cta ttt gaa gga ttc tgatcataaa cataataagg agtatatata tattactcca     1203
Leu Phe Glu Gly Phe
    310 actatattat aaagcttaaa taagaggccg tgttaattag tacttgttgc cttttgcttt   1263 atggtgttgt ttattatgcc ttgtatgctt gtaatattat ctagagaaca agatgtactg   1323 tgtaatagtc ttgtttgaaa taaaacttcc aattatgatg caaaaaaaaa aaaaaa       1379

<210> SEQ ID NO 22
<211> LENGTH: 313
<212> TYPE: PRT
<213> ORGANISM: Phytolacca americana

<400> SEQUENCE: 22

Met Lys Ser Met Leu Val Val Thr Ile Ser Ile Trp Leu Ile Leu Ala
1               5                   10                  15

Pro Thr Ser Thr Trp Ala Val Asn Thr Ile Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
```

```
                50                  55                  60
Thr Asn Thr Asn Pro Lys Tyr Val Leu Val Glu Leu Gln Gly Ser Asn
 65                  70                  75                  80

Lys Lys Thr Ile Thr Leu Met Leu Arg Arg Asn Asn Leu Tyr Val Met
                 85                  90                  95

Gly Tyr Ser Asp Pro Phe Glu Thr Asn Lys Cys Arg Tyr His Ile Phe
            100                 105                 110

Asn Asp Ile Ser Gly Thr Glu Arg Gln Asp Val Glu Thr Thr Leu Cys
        115                 120                 125

Pro Asn Ala Asn Ser Arg Val Ser Lys Asn Ile Asn Phe Asp Ser Arg
130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Leu Ala Tyr Val Gly Gly Ser Cys Gln Thr Thr Tyr Asn Gln Asn
        275                 280                 285

Ala Met Phe Pro Gln Leu Ile Met Ser Thr Tyr Tyr Asn Tyr Met Val
    290                 295                 300

Asn Leu Gly Asp Leu Phe Glu Gly Phe
305                 310

<210> SEQ ID NO 23
<211> LENGTH: 1379
<212> TYPE: DNA
<213> ORGANISM: Phytolacca americana
<220> FEATURE:
<221> NAME/KEY: CDS
<222> LOCATION: (225)..(1163)

<400> SEQUENCE: 23
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                               Met Lys Ser Met
                                                 1 ctt gtg gtg aca ata tca ata tgg ctc att ctt gca cca act tca act     284
Leu Val Val Thr Ile Ser Ile Trp Leu Ile Leu Ala Pro Thr Ser Thr
  5                  10                  15                  20 tgg gct gtg aat aca atc atc tac aat gtt gga agt acc acc att agc     332
Trp Ala Val Asn Thr Ile Ile Tyr Asn Val Gly Ser Thr Thr Ile Ser
                 25                  30                  35 aaa tac gcc act ttt ctg aat gat ctt cgt aat gaa gcg aaa gat cca     380
```

-continued

| | | |
|---|---|---|
| Lys Tyr Ala Thr Phe Leu Asn Asp Leu Arg Asn Glu Ala Lys Asp Pro<br>40                             45                            50 | | |
| agt tta aaa tgc tat gga ata cca atg ctg ccc aat aca aat aca aat<br>Ser Leu Lys Cys Tyr Gly Ile Pro Met Leu Pro Asn Thr Asn Thr Asn<br>        55                       60                        65 | | 428 |
| cca aag tac gtg ttg gtt gag ctc caa ggt tca aat aaa aaa acc atc<br>Pro Lys Tyr Val Leu Val Glu Leu Gln Gly Ser Asn Lys Lys Thr Ile<br>70                         75                       80 | | 476 |
| aca cta atg ctg aga cga aac aat ttg tat gtg atg ggt tat tct gat<br>Thr Leu Met Leu Arg Arg Asn Asn Leu Tyr Val Met Gly Tyr Ser Asp<br>85                       90                       95                     100 | | 524 |
| ccc ttt gaa acc aat aaa tgt cgt tac cat atc ttt aat gat atc tca<br>Pro Phe Glu Thr Asn Lys Cys Arg Tyr His Ile Phe Asn Asp Ile Ser<br>                       105                       110                     115 | | 572 |
| ggt act gaa cgc caa gat gta gag act act ctt tgc cca aat gcc aat<br>Gly Thr Glu Arg Gln Asp Val Glu Thr Thr Leu Cys Pro Asn Ala Asn<br>               120                       125                     130 | | 620 |
| tct cgt gtt agt aaa aac ata aac ttt gat agt cga tat cca aca ttg<br>Ser Arg Val Ser Lys Asn Ile Asn Phe Asp Ser Arg Tyr Pro Thr Leu<br>           135                       140                     145 | | 668 |
| gaa tca aaa gcg gga gta aaa tca aga agt cag gtc caa ctg gga att<br>Glu Ser Lys Ala Gly Val Lys Ser Arg Ser Gln Val Gln Leu Gly Ile<br>150                       155                       160 | | 716 |
| caa ata ctc gac agt aat att gga aag att tct gga gtg atg tca ttc<br>Gln Ile Leu Asp Ser Asn Ile Gly Lys Ile Ser Gly Val Met Ser Phe<br>165                       170                       175                     180 | | 764 |
| act gag aaa acc gaa gcc gaa ttc cta ttg gta gcc ata caa atg gta<br>Thr Glu Lys Thr Glu Ala Glu Phe Leu Leu Val Ala Ile Gln Met Val<br>               185                       190                     195 | | 812 |
| tca gag gca gca aga ttc aag tac ata gag aat cag gtg aaa act aat<br>Ser Glu Ala Ala Arg Phe Lys Tyr Ile Glu Asn Gln Val Lys Thr Asn<br>           200                       205                     210 | | 860 |
| ttt aac aga gca ttc aac cct aat ccc aaa gta ctt aat ttg caa gag<br>Phe Asn Arg Ala Phe Asn Pro Asn Pro Lys Val Leu Asn Leu Gln Glu<br>           215                       220                     225 | | 908 |
| aca tgg ggt aag att tca aca gca att cat gat gcc aag aat gga gtt<br>Thr Trp Gly Lys Ile Ser Thr Ala Ile His Asp Ala Lys Asn Gly Val<br>230                       235                       240 | | 956 |
| tta ccc aaa cct ctc gag cta gtg gat gcc agt ggt gcc aag tgg ata<br>Leu Pro Lys Pro Leu Glu Leu Val Asp Ala Ser Gly Ala Lys Trp Ile<br>245                       250                       255                     260 | | 1004 |
| gtg ttg aga gtg gat gaa atc aag cct gat gta gca ctc tta gca tac<br>Val Leu Arg Val Asp Glu Ile Lys Pro Asp Val Ala Leu Leu Ala Tyr<br>               265                       270                     275 | | 1052 |
| gtt ggt ggg agc tgt cag aca act tat aac caa aat gcc atg ttt cct<br>Val Gly Gly Ser Cys Gln Thr Thr Tyr Asn Gln Asn Ala Met Phe Pro<br>           280                       285                     290 | | 1100 |
| caa ctt ata atg tct act tat tat aat tac atg gtt aat ctt ggt gat<br>Gln Leu Ile Met Ser Thr Tyr Tyr Asn Tyr Met Val Asn Leu Gly Asp<br>           295                       300                     305 | | 1148 |
| cta ttt gaa gga ttc tgatcataaa cataataagg agtatatata tattactcca<br>Leu Phe Glu Gly Phe<br>    310 | | 1203 |
| actatattat aaagcttaaa taagaggccg tgttaattag tacttgttgc cttttgcttt | | 1263 |
| atggtgttgt ttattatgcc ttgtatgctt gtaatattat ctagagaaca agatgtactg | | 1323 |
| tgtaatagtc ttgtttgaaa taaaacttcc aattatgatg caaaaaaaaa aaaaaa | | 1379 |

<210> SEQ ID NO 24
<211> LENGTH: 1379

<212> TYPE: DNA
<213> ORGANISM: Phytolacca americana
<220> FEATURE:
<221> NAME/KEY: CDS
<222> LOCATION: (225)..(1163)

<400> SEQUENCE: 24

```
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                                Met Lys Ser Met
                                                  1 ctt gtg gtg aca ata tca ata tgg ctc att ctt gca cca act tca act      284
Leu Val Val Thr Ile Ser Ile Trp Leu Ile Leu Ala Pro Thr Ser Thr
  5              10                  15                  20 tgg gct gtg aat aca atc atc tac aat gtt gga agt acc acc att agc      332
Trp Ala Val Asn Thr Ile Ile Tyr Asn Val Gly Ser Thr Thr Ile Ser
             25                  30                  35 aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
         40                  45                  50 agt tta aaa tgc tat gga ata cca atg ctg ccc aat aca aat aca aat      428
Ser Leu Lys Cys Tyr Gly Ile Pro Met Leu Pro Asn Thr Asn Thr Asn
     55                  60                  65 cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
 70                  75                  80 aca cta atg ctg aga cga aac aat ttg tat gtg atg ggt tat tct gat      524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
            120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
    230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
```

```
              245                 250                 255                 260
gtg ttg aga gtg gat gaa atc aag cct gat gta gca ctc tta aga tac         1052
Val Leu Arg Val Asp Glu Ile Lys Pro Asp Val Ala Leu Leu Arg Tyr
                265                 270                 275 gtt ggt ggg agc tgt cag aca act tat aac caa aat gcc atg ttt cct         1100
Val Gly Gly Ser Cys Gln Thr Thr Tyr Asn Gln Asn Ala Met Phe Pro
            280                 285                 290 caa ctt ata atg tct act tat tat aat tac atg gtt aat ctt ggt gat         1148
Gln Leu Ile Met Ser Thr Tyr Tyr Asn Tyr Met Val Asn Leu Gly Asp
                295                 300                 305 cta ttt gaa gga ttc tgatcataaa cataataagg agtatatata tattactcca         1203
Leu Phe Glu Gly Phe
        310 actatattat aaagcttaaa taagaggccg tgttaattag tacttgttgc cttttgcttt       1263 atggtgttgt ttattatgcc ttgtatgctt gtaatattat ctagagaaca agatgtactg       1323 tgtaatagtc ttgtttgaaa taaaacttcc aattatgatg caaaaaaaaa aaaaaa           1379

<210> SEQ ID NO 25
<211> LENGTH: 313
<212> TYPE: PRT
<213> ORGANISM: Phytolacca americana

<400> SEQUENCE: 25

Met Lys Ser Met Leu Val Val Thr Ile Ser Ile Trp Leu Ile Leu Ala
 1               5                  10                  15

Pro Thr Ser Thr Trp Ala Val Asn Thr Ile Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
    50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
            100                 105                 110

Asn Asp Ile Ser Gly Thr Glu Arg Gln Asp Val Glu Thr Thr Leu Cys
        115                 120                 125

Pro Asn Ala Asn Ser Arg Val Ser Lys Asn Ile Asn Phe Asp Ser Arg
    130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
    210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255
```

```
Ala Lys Trp Ile Val Leu Arg Val Asp Glu Ile Lys Pro Asp Val Ala
            260                 265                 270

Leu Leu Arg Tyr Val Gly Gly Ser Cys Gln Thr Thr Tyr Asn Gln Asn
            275                 280                 285

Ala Met Phe Pro Gln Leu Ile Met Ser Thr Tyr Tyr Asn Tyr Met Val
            290                 295                 300

Asn Leu Gly Asp Leu Phe Glu Gly Phe
305                 310

<210> SEQ ID NO 26
<211> LENGTH: 1379
<212> TYPE: DNA
<213> ORGANISM: Phytolacca americana
<220> FEATURE:
<221> NAME/KEY: CDS
<222> LOCATION: (225)..(1163)

<400> SEQUENCE: 26
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                              Met Lys Ser Met
                                                1 ctt gtg gtg aca ata tca ata tgg ctc att ctt gca cca act tca act     284
Leu Val Val Thr Ile Ser Ile Trp Leu Ile Leu Ala Pro Thr Ser Thr
  5              10                  15                  20 tgg gct gtg aat aca atc atc tac aat gtt gga agt acc acc att agc     332
Trp Ala Val Asn Thr Ile Ile Tyr Asn Val Gly Ser Thr Thr Ile Ser
             25                  30                  35 aaa tac gcc act ttt ctg aat gat ctt cgt aat gaa gcg aaa gat cca     380
Lys Tyr Ala Thr Phe Leu Asn Asp Leu Arg Asn Glu Ala Lys Asp Pro
         40                  45                  50 agt tta aaa tgc tat gga ata cca atg ctg ccc aat aca aat aca aat     428
Ser Leu Lys Cys Tyr Gly Ile Pro Met Leu Pro Asn Thr Asn Thr Asn
     55                  60                  65 cca aag tac gtg ttg gtt gag ctc caa ggt tca aat aaa aaa acc atc     476
Pro Lys Tyr Val Leu Val Glu Leu Gln Gly Ser Asn Lys Lys Thr Ile
 70                  75                  80 aca cta atg ctg aga cga aac aat ttg tat gtg atg ggt tat tct gat     524
Thr Leu Met Leu Arg Arg Asn Asn Leu Tyr Val Met Gly Tyr Ser Asp
             85                  90                  95             100 ccc ttt gaa acc aat aaa tgt cgt tac cat atc ttt aat gat atc tca     572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat     620
Gly Thr Glu Arg Gln Asp Val Glu Thr Thr Leu Cys Pro Asn Ala Asn
         120                 125                 130 tct cgt gtt agt aaa aac ata aac ttt gat agt cga tat cca aca ttg     668
Ser Arg Val Ser Lys Asn Ile Asn Phe Asp Ser Arg Tyr Pro Thr Leu
     135                 140                 145 gaa tca aaa gcg gga gta aaa tca aga agt cag gtc caa ctg gga att     716
Glu Ser Lys Ala Gly Val Lys Ser Arg Ser Gln Val Gln Leu Gly Ile
 150                 155                 160 caa ata ctc gac agt aat att gga aag att tct gga gtg atg tca ttc     764
Gln Ile Leu Asp Ser Asn Ile Gly Lys Ile Ser Gly Val Met Ser Phe
             165                 170                 175             180 act gag aaa acc gaa gcc gaa ttc cta ttg gta gcc ata caa atg gta     812
Thr Glu Lys Thr Glu Ala Glu Phe Leu Leu Val Ala Ile Gln Met Val
                185                 190                 195
```

```
tca gag gca gca aga ttc aag tac ata gag aat cag gtg aaa act aat      860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
    230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta agg tac     1052
Val Leu Arg Val Asp Glu Ile Lys Pro Asp Val Ala Leu Leu Arg Tyr
                265                 270                 275 gtt ggt ggg agc tgt cag aca act tat aac caa aat gcc atg ttt cct     1100
Val Gly Gly Ser Cys Gln Thr Thr Tyr Asn Gln Asn Ala Met Phe Pro
            280                 285                 290 caa ctt ata atg tct act tat tat aat tac atg gtt aat ctt ggt gat     1148
Gln Leu Ile Met Ser Thr Tyr Tyr Asn Tyr Met Val Asn Leu Gly Asp
        295                 300                 305 cta ttt gaa gga ttc tgatcataaa cataataagg agtatatata tattactcca     1203
Leu Phe Glu Gly Phe
    310 actatattat aaagcttaaa taagaggccg tgttaattag tacttgttgc cttttgcttt   1263 atggtgttgt ttattatgcc ttgtatgctt gtaatattat ctagagaaca agatgtactg   1323 tgtaatagtc ttgtttgaaa taaaacttcc aattatgatg caaaaaaaaa aaaaaa       1379

<210> SEQ ID NO 27
<211> LENGTH: 1379
<212> TYPE: DNA
<213> ORGANISM: Phytolacca americana
<220> FEATURE:
<221> NAME/KEY: CDS
<222> LOCATION: (225)..(1163)

<400> SEQUENCE: 27
ctatgaagtc gggtcaaagc atatacaggc tatgcattgt tagaaacatt gatgcctctg    60
atcccgataa acaatacaaa ttagacaata agatgacata caagtaccta aactgtgtat   120
gggggagtga aacctcagct gctaaaaaaa cgttgtaaga aaaaaagaaa gttgtgagtt   180
aactacaggg cgaaagtatt ggaactagct agtaggaagg gaag atg aag tcg atg    236
                                                 Met Lys Ser Met
                                                   1 ctt gtg gtg aca ata tca ata tgg ctc att ctt gca cca act tca act     284
Leu Val Val Thr Ile Ser Ile Trp Leu Ile Leu Ala Pro Thr Ser Thr
  5                  10                  15                  20 tgg gct gtg aat aca atc atc tac aat gtt gga agt acc acc att agc     332
Trp Ala Val Asn Thr Ile Ile Tyr Asn Val Gly Ser Thr Thr Ile Ser
             25                  30                  35 aaa tac gcc act ttt ctg aat gat ctt cgt aat gaa gcg aaa gat cca     380
Lys Tyr Ala Thr Phe Leu Asn Asp Leu Arg Asn Glu Ala Lys Asp Pro
         40                  45                  50 agt tta aaa tgc tat gga ata cca atg ctg ccc aat aca aat aca aat     428
Ser Leu Lys Cys Tyr Gly Ile Pro Met Leu Pro Asn Thr Asn Thr Asn
     55                  60                  65 cca aag tac gtg ttg gtt gag ctc caa ggt tca aat aaa aaa acc atc     476
Pro Lys Tyr Val Leu Val Glu Leu Gln Gly Ser Asn Lys Lys Thr Ile
 70                  75                  80
```

```
aca cta atg ctg aga cga aac aat ttg tat gtg atg ggt tat tct gat      524
Thr Leu Met Leu Arg Arg Asn Asn Leu Tyr Val Met Gly Tyr Ser Asp
 85              90                  95                 100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
            120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
    230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc aaa gcc tac     1052
Val Leu Arg Val Asp Glu Ile Lys Pro Asp Val Ala Leu Lys Ala Tyr
                265                 270                 275 gtt ggt ggg agc tgt cag aca act tat aac caa aat gcc atg ttt cct     1100
Val Gly Gly Ser Cys Gln Thr Thr Tyr Asn Gln Asn Ala Met Phe Pro
            280                 285                 290 caa ctt ata atg tct act tat tat aat tac atg gtt aat ctt ggt gat     1148
Gln Leu Ile Met Ser Thr Tyr Tyr Asn Tyr Met Val Asn Leu Gly Asp
        295                 300                 305 cta ttt gaa gga ttc tgatcataaa cataataagg agtatatata tattactcca     1203
Leu Phe Glu Gly Phe
    310 actatattat aaagcttaaa taagaggccg tgttaattag tacttgttgc cttttgcttt   1263 atggtgttgt ttattatgcc ttgtatgctt gtaatattat ctagagaaca agatgtactg   1323 tgtaatagtc ttgtttgaaa taaaacttcc aattatgatg caaaaaaaaa aaaaaa       1379

<210> SEQ ID NO 28
<211> LENGTH: 313
<212> TYPE: PRT
<213> ORGANISM: Phytolacca americana

<400> SEQUENCE: 28

Met Lys Ser Met Leu Val Val Thr Ile Ser Ile Trp Leu Ile Leu Ala
 1               5                  10                  15

Pro Thr Ser Thr Trp Ala Val Asn Thr Ile Ile Tyr Asn Val Gly Ser
            20                  25                  30
```

Thr Thr Ile Ser Lys Tyr Ala Thr Phe Leu Asn Asp Leu Arg Asn Glu
         35                  40                  45

Ala Lys Asp Pro Ser Leu Lys Cys Tyr Gly Ile Pro Met Leu Pro Asn
 50                  55                  60

Thr Asn Thr Asn Pro Lys Tyr Val Leu Val Glu Leu Gln Gly Ser Asn
 65                  70                  75                  80

Lys Lys Thr Ile Thr Leu Met Leu Arg Arg Asn Asn Leu Tyr Val Met
                 85                  90                  95

Gly Tyr Ser Asp Pro Phe Glu Thr Asn Lys Cys Arg Tyr His Ile Phe
                100                 105                 110

Asn Asp Ile Ser Gly Thr Glu Arg Gln Asp Val Glu Thr Thr Leu Cys
            115                 120                 125

Pro Asn Ala Asn Ser Arg Val Ser Lys Asn Ile Asn Phe Asp Ser Arg
130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Lys Ala Tyr Val Gly Gly Ser Cys Gln Thr Thr Tyr Asn Gln Asn
        275                 280                 285

Ala Met Phe Pro Gln Leu Ile Met Ser Thr Tyr Tyr Asn Tyr Met Val
290                 295                 300

Asn Leu Gly Asp Leu Phe Glu Gly Phe
305                 310

<210> SEQ ID NO 29
<211> LENGTH: 1379
<212> TYPE: DNA
<213> ORGANISM: Phytolacca americana
<220> FEATURE:
<221> NAME/KEY: CDS
<222> LOCATION: (225)..(1163)

<400> SEQUENCE: 29
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                              Met Lys Ser Met
                                                1 ctt gtg gtg aca ata tca ata tgg ctc att ctt gca cca act tca act     284
Leu Val Val Thr Ile Ser Ile Trp Leu Ile Leu Ala Pro Thr Ser Thr
  5                  10                  15                  20 tgg gct gtg aat aca atc atc tac aat gtt gga agt acc acc att agc     332

```
Trp Ala Val Asn Thr Ile Ile Tyr Asn Val Gly Ser Thr Thr Ile Ser
            25                  30                  35 aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
                40                  45                  50 agt tta aaa tgc tat gga ata cca atg ctg ccc aat aca aat aca aat      428
Ser Leu Lys Cys Tyr Gly Ile Pro Met Leu Pro Asn Thr Asn Thr Asn
        55                  60                  65 cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
    70                  75                  80 aca cta atg ctg aga cga aac aat ttg tat gtg atg ggt tat tct gat      524
Thr Leu Met Leu Arg Arg Asn Asn Leu Tyr Val Met Gly Tyr Ser Asp
85                  90                  95                  100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
                120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
                200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
    230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc aag gca tac     1052
Val Leu Arg Val Asp Glu Ile Lys Pro Asp Val Ala Leu Lys Ala Tyr
                265                 270                 275 gtt ggt ggg agc tgt cag aca act tat aac caa aat gcc atg ttt cct     1100
Val Gly Gly Ser Cys Gln Thr Thr Tyr Asn Gln Asn Ala Met Phe Pro
                280                 285                 290 caa ctt ata atg tct act tat tat aat tac atg gtt aat ctt ggt gat     1148
Gln Leu Ile Met Ser Thr Tyr Tyr Asn Tyr Met Val Asn Leu Gly Asp
        295                 300                 305 cta ttt gaa gga ttc tgatcataaa cataataagg agtatatata tattactcca     1203
Leu Phe Glu Gly Phe
    310 actatattat aaagcttaaa taagaggccg tgttaattag tacttgttgc cttttgcttt     1263 atggtgttgt ttattatgcc ttgtatgctt gtaatattat ctagagaaca agatgtactg     1323 tgtaatagtc ttgtttgaaa taaaacttcc aattatgatg caaaaaaaaa aaaaaa         1379
```

<210> SEQ ID NO 30
<211> LENGTH: 1052
<212> TYPE: DNA
<213> ORGANISM: Phytolacca americana
<220> FEATURE:
<221> NAME/KEY: CDS
<222> LOCATION: (225)..(1049)

<400> SEQUENCE: 30

```
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                               Met Lys Ser Met
                                                 1 ctt gtg gtg aca ata tca ata tgg ctc att ctt gca cca act tca act     284
Leu Val Val Thr Ile Ser Ile Trp Leu Ile Leu Ala Pro Thr Ser Thr
  5                  10                  15                  20 tgg gct gtg aat aca atc atc tac aat gtt gga agt acc acc att agc     332
Trp Ala Val Asn Thr Ile Ile Tyr Asn Val Gly Ser Thr Thr Ile Ser
                 25                  30                  35 aaa tac gcc act ttt ctg aat gat ctt cgt aat gaa gcg aaa gat cca     380
Lys Tyr Ala Thr Phe Leu Asn Asp Leu Arg Asn Glu Ala Lys Asp Pro
             40                  45                  50 agt tta aaa tgc tat gga ata cca atg ctg ccc aat aca aat aca aat     428
Ser Leu Lys Cys Tyr Gly Ile Pro Met Leu Pro Asn Thr Asn Thr Asn
         55                  60                  65 cca aag tac gtg ttg gtt gag ctc caa ggt tca aat aaa aaa acc atc     476
Pro Lys Tyr Val Leu Val Glu Leu Gln Gly Ser Asn Lys Lys Thr Ile
     70                  75                  80 aca cta atg ctg aga cga aac aat ttg tat gtg atg ggt tat tct gat     524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca     572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat     620
Gly Thr Glu Arg Gln Asp Val Glu Thr Thr Leu Cys Pro Asn Ala Asn
            120                 125                 130 tct cgt gtt agt aaa aac ata aac ttt gat agt cga tat cca aca ttg     668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att     716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc     764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta     812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat     860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag     908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt     956
Thr Trp Gly Lys Ile Ser Thr Ala Ile His Asp Ala Lys Asn Gly Val
```

```
                230                 235                 240
tta ccc aaa cct ctc gag cta gtg gat gcc agt ggt gcc aag tgg ata         1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta gcc taa         1052
Val Leu Arg Val Asp Glu Ile Lys Pro Asp Val Ala Leu Leu Ala
                265                 270                 275

<210> SEQ ID NO 31
<211> LENGTH: 275
<212> TYPE: PRT
<213> ORGANISM: Phytolacca americana

<400> SEQUENCE: 31

Met Lys Ser Met Leu Val Val Thr Ile Ser Ile Trp Leu Ile Leu Ala
 1               5                  10                  15

Pro Thr Ser Thr Trp Ala Val Asn Thr Ile Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
    50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
           100                 105                 110

Asn Asp Ile Ser Gly Thr Glu Arg Gln Asp Val Glu Thr Thr Leu Cys
       115                 120                 125

Pro Asn Ala Asn Ser Arg Val Ser Lys Asn Ile Asn Phe Asp Ser Arg
   130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
           180                 185                 190

Ile Gln Met Val Ser Glu Ala Ala Arg Phe Lys Tyr Ile Glu Asn Gln
       195                 200                 205

Val Lys Thr Asn Phe Asn Arg Ala Phe Asn Pro Asn Pro Lys Val Leu
   210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
           260                 265                 270

Leu Leu Ala
       275

<210> SEQ ID NO 32
<211> LENGTH: 1052
<212> TYPE: DNA
<213> ORGANISM: Phytolacca americana
<220> FEATURE:
<221> NAME/KEY: CDS
<222> LOCATION: (225)..(1049)
```

<400> SEQUENCE: 32

```
ctatgaagtc gggtcaaagc atatacaggc tatgcattgt tagaaacatt gatgcctctg    60
atcccgataa acaatacaaa ttagacaata agatgacata caagtaccta aactgtgtat   120
gggggagtga aacctcagct gctaaaaaaa cgttgtaaga aaaaagaaa gttgtgagtt    180 aactacaggg cgaaagtatt ggaactagct agtaggaagg gaag atg aag tcg atg    236
                                              Met Lys Ser Met
                                               1 ctt gtg gtg aca ata tca ata tgg ctc att ctt gca cca act tca act    284
Leu Val Val Thr Ile Ser Ile Trp Leu Ile Leu Ala Pro Thr Ser Thr
  5              10                  15                  20 tgg gct gtg aat aca atc atc tac aat gtt gga agt acc acc att agc    332
Trp Ala Val Asn Thr Ile Ile Tyr Asn Val Gly Ser Thr Thr Ile Ser
             25                  30                  35 aaa tac gcc act ttt ctg aat gat ctt cgt aat gaa gcg aaa gat cca    380
Lys Tyr Ala Thr Phe Leu Asn Asp Leu Arg Asn Glu Ala Lys Asp Pro
         40                  45                  50 agt tta aaa tgc tat gga ata cca atg ctg ccc aat aca aat aca aat    428
Ser Leu Lys Cys Tyr Gly Ile Pro Met Leu Pro Asn Thr Asn Thr Asn
     55                  60                  65 cca aag tac gtg ttg gtt gag ctc caa ggt tca aat aaa aaa acc atc    476
Pro Lys Tyr Val Leu Val Glu Leu Gln Gly Ser Asn Lys Lys Thr Ile
 70                  75                  80 aca cta atg ctg aga cga aac aat ttg tat gtg atg ggt tat tct gat    524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca    572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat    620
Gly Thr Glu Arg Gln Asp Val Glu Thr Thr Leu Cys Pro Asn Ala Asn
            120                 125                 130 tct cgt gtt agt aaa aac ata aac ttt gat agt cga tat cca aca ttg    668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att    716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc    764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta    812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat    860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag    908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt    956
Thr Trp Gly Lys Ile Ser Thr Ala Ile His Asp Ala Lys Asn Gly Val
    230                 235                 240 tta ccc aaa cct ctc gag cta gtg gat gcc agt ggt gcc aag tgg ata   1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta gca taa   1052
Val Leu Arg Val Asp Glu Ile Lys Pro Asp Val Ala Leu Leu Ala
                265                 270                 275
```

<210> SEQ ID NO 33
<211> LENGTH: 1052
<212> TYPE: DNA
<213> ORGANISM: Phytolacca americana
<220> FEATURE:
<221> NAME/KEY: CDS
<222> LOCATION: (225)..(1049)

<400> SEQUENCE: 33

| | |
|---|---|
| ctatgaagtc gggtcaaagc atatacaggc tatgcattgt tagaaacatt gatgcctctg | 60 |
| atcccgataa acaatacaaa ttagacaata agatgacata caagtaccta aactgtgtat | 120 |
| ggggagtga aacctcagct gctaaaaaaa cgttgtaaga aaaaagaaa gttgtgagtt | 180 |
| aactacaggg cgaaagtatt ggaactagct agtaggaagg gaag atg aag tcg atg | 236 |
|                                                                                              Met Lys Ser Met<br>                                                                                              1 | |
| ctt gtg gtg aca ata tca ata tgg ctc att ctt gca cca act tca act<br>Leu Val Val Thr Ile Ser Ile Trp Leu Ile Leu Ala Pro Thr Ser Thr<br>5                    10                   15                   20 | 284 |
| tgg gct gtg aat aca atc atc tac aat gtt gga agt acc acc att agc<br>Trp Ala Val Asn Thr Ile Ile Tyr Asn Val Gly Ser Thr Thr Ile Ser<br>             25                   30                   35 | 332 |
| aaa tac gcc act ttt ctg aat gat ctt cgt aat gaa gcg aaa gat cca<br>Lys Tyr Ala Thr Phe Leu Asn Asp Leu Arg Asn Glu Ala Lys Asp Pro<br>40                    45                   50 | 380 |
| agt tta aaa tgc tat gga ata cca atg ctg ccc aat aca aat aca aat<br>Ser Leu Lys Cys Tyr Gly Ile Pro Met Leu Pro Asn Thr Asn Thr Asn<br>             55                   60                   65 | 428 |
| cca aag tac gtg ttg gtt gag ctc caa ggt tca aat aaa aaa acc atc<br>Pro Lys Tyr Val Leu Val Glu Leu Gln Gly Ser Asn Lys Lys Thr Ile<br>70                    75                   80 | 476 |
| aca cta atg ctg aga cga aac aat ttg tat gtg atg ggt tat tct gat<br>Thr Leu Met Leu Arg Arg Asn Asn Leu Tyr Val Met Gly Tyr Ser Asp<br>85                    90                   95                 100 | 524 |
| ccc ttt gaa acc aat aaa tgt cgt tac cat atc ttt aat gat atc tca<br>Pro Phe Glu Thr Asn Lys Cys Arg Tyr His Ile Phe Asn Asp Ile Ser<br>             105                 110                 115 | 572 |
| ggt act gaa cgc caa gat gta gag act act ctt tgc cca aat gcc aat<br>Gly Thr Glu Arg Gln Asp Val Glu Thr Thr Leu Cys Pro Asn Ala Asn<br>120                  125                 130 | 620 |
| tct cgt gtt agt aaa aac ata aac ttt gat agt cga tat cca aca ttg<br>Ser Arg Val Ser Lys Asn Ile Asn Phe Asp Ser Arg Tyr Pro Thr Leu<br>             135                 140                 145 | 668 |
| gaa tca aaa gcg gga gta aaa tca aga agt cag gtc caa ctg gga att<br>Glu Ser Lys Ala Gly Val Lys Ser Arg Ser Gln Val Gln Leu Gly Ile<br>150                  155                 160 | 716 |
| caa ata ctc gac agt aat att gga aag att tct gga gtg atg tca ttc<br>Gln Ile Leu Asp Ser Asn Ile Gly Lys Ile Ser Gly Val Met Ser Phe<br>165                  170                 175                 180 | 764 |
| act gag aaa acc gaa gcc gaa ttc cta ttg gta gcc ata caa atg gta<br>Thr Glu Lys Thr Glu Ala Glu Phe Leu Leu Val Ala Ile Gln Met Val<br>                  185                 190                 195 | 812 |
| tca gag gca gca aga ttc aag tac ata gag aat cag gtg aaa act aat<br>Ser Glu Ala Ala Arg Phe Lys Tyr Ile Glu Asn Gln Val Lys Thr Asn<br>200                  205                 210 | 860 |
| ttt aac aga gca ttc aac cct aat ccc aaa gta ctt aat ttg caa gag<br>Phe Asn Arg Ala Phe Asn Pro Asn Pro Lys Val Leu Asn Leu Gln Glu<br>             215                 220                 225 | 908 |
| aca tgg ggt aag att tca aca gca att cat gat gcc aag aat gga gtt<br>Thr Trp Gly Lys Ile Ser Thr Ala Ile His Asp Ala Lys Asn Gly Val | 956 |

```
                  230                 235                 240
tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta aga taa     1052
Val Leu Arg Val Asp Glu Ile Lys Pro Asp Val Ala Leu Leu Arg
                265                 270                 275

<210> SEQ ID NO 34
<211> LENGTH: 275
<212> TYPE: PRT
<213> ORGANISM: Phytolacca americana

<400> SEQUENCE: 34

Met Lys Ser Met Leu Val Val Thr Ile Ser Ile Trp Leu Ile Leu Ala
 1               5                  10                  15

Pro Thr Ser Thr Trp Ala Val Asn Thr Ile Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
    50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
            100                 105                 110

Asn Asp Ile Ser Gly Thr Glu Arg Gln Asp Val Glu Thr Thr Leu Cys
        115                 120                 125

Pro Asn Ala Asn Ser Arg Val Ser Lys Asn Ile Asn Phe Asp Ser Arg
    130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
    210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Leu Arg
        275

<210> SEQ ID NO 35
<211> LENGTH: 1052
<212> TYPE: DNA
<213> ORGANISM: Phytolacca americana
<220> FEATURE:
<221> NAME/KEY: CDS
<222> LOCATION: (225)..(1049)
```

<400> SEQUENCE: 35

```
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                               Met Lys Ser Met
                                                 1 ctt gtg gtg aca ata tca ata tgg ctc att ctt gca cca act tca act      284
Leu Val Val Thr Ile Ser Ile Trp Leu Ile Leu Ala Pro Thr Ser Thr
  5                  10                  15                  20 tgg gct gtg aat aca atc atc tac aat gtt gga agt acc acc att agc      332
Trp Ala Val Asn Thr Ile Ile Tyr Asn Val Gly Ser Thr Thr Ile Ser
                 25                  30                  35 aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
 40                  45                  50 agt tta aaa tgc tat gga ata cca atg ctg ccc aat aca aat aca aat      428
Ser Leu Lys Cys Tyr Gly Ile Pro Met Leu Pro Asn Thr Asn Thr Asn
         55                  60                  65 cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
 70                  75                  80 aca cta atg ctg aga cga aac aat ttg tat gtg atg ggt tat tct gat      524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                 105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
         120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
        200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta agg taa     1052
Val Leu Arg Val Asp Glu Ile Lys Pro Asp Val Ala Leu Leu Arg
                265                 270                 275
```

<210> SEQ ID NO 36
<211> LENGTH: 1052
<212> TYPE: DNA
<213> ORGANISM: Phytolacca americana
<220> FEATURE:
<221> NAME/KEY: CDS
<222> LOCATION: (225)..(1049)

<400> SEQUENCE: 36

```
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg      236
                                                Met Lys Ser Met
                                                 1 ctt gtg gtg aca ata tca ata tgg ctc att ctt gca cca act tca act      284
Leu Val Val Thr Ile Ser Ile Trp Leu Ile Leu Ala Pro Thr Ser Thr
  5              10                  15                  20 tgg gct gtg aat aca atc atc tac aat gtt gga agt acc acc att agc      332
Trp Ala Val Asn Thr Ile Ile Tyr Asn Val Gly Ser Thr Thr Ile Ser
              25                  30                  35 aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
          40                  45                  50 agt tta aaa tgc tat gga ata cca atg ctg ccc aat aca aat aca aat      428
Ser Leu Lys Cys Tyr Gly Ile Pro Met Leu Pro Asn Thr Asn Thr Asn
      55                  60                  65 cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
  70                  75                  80 aca cta atg ctg aga cga aac aat ttg tat gtg atg ggt tat tct gat      524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
            120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
        135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
```

```
                   230                 235                 240
tta ccc aaa cct ctc gag cta gtg gat gcc agt ggt gcc aag tgg ata      1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta gat taa      1052
Val Leu Arg Val Asp Glu Ile Lys Pro Asp Val Ala Leu Leu Asp
                265                 270                 275

<210> SEQ ID NO 37
<211> LENGTH: 275
<212> TYPE: PRT
<213> ORGANISM: Phytolacca americana

<400> SEQUENCE: 37

Met Lys Ser Met Leu Val Val Thr Ile Ser Ile Trp Leu Ile Leu Ala
 1               5                  10                  15

Pro Thr Ser Thr Trp Ala Val Asn Thr Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
    50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
            100                 105                 110

Asn Asp Ile Ser Gly Thr Glu Arg Gln Asp Val Glu Thr Thr Leu Cys
        115                 120                 125

Pro Asn Ala Asn Ser Arg Val Ser Lys Asn Ile Asn Phe Asp Ser Arg
    130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
    210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Leu Asp
        275

<210> SEQ ID NO 38
<211> LENGTH: 1052
<212> TYPE: DNA
<213> ORGANISM: Phytolacca americana
<220> FEATURE:
<221> NAME/KEY: CDS
<222> LOCATION: (225)..(1049)
```

<400> SEQUENCE: 38

```
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaagaaa gttgtgagtt      180 aactacaggg cgaaagtatt ggaactagct agtaggaagg gaag atg aag tcg atg     236
                                                Met Lys Ser Met
                                                  1 ctt gtg gtg aca ata tca ata tgg ctc att ctt gca cca act tca act      284
Leu Val Val Thr Ile Ser Ile Trp Leu Ile Leu Ala Pro Thr Ser Thr
  5              10                  15                  20 tgg gct gtg aat aca atc atc tac aat gtt gga agt acc acc att agc      332
Trp Ala Val Asn Thr Ile Ile Tyr Asn Val Gly Ser Thr Thr Ile Ser
             25                  30                  35 aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
         40                  45                  50 agt tta aaa tgc tat gga ata cca atg ctg ccc aat aca aat aca aat     428
Ser Leu Lys Cys Tyr Gly Ile Pro Met Leu Pro Asn Thr Asn Thr Asn
     55                  60                  65 cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
 70                  75                  80 aca cta atg ctg aga cga aac aat ttg tat gtg atg ggt tat tct gat      524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
             105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
         120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
     135                 140                 145 gaa tca aaa gcg gga gta aaa tca aga agt cag gtc caa ctg gga att      716
Glu Ser Lys Ala Gly Val Lys Ser Arg Ser Gln Val Gln Leu Gly Ile
 150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
             185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
         200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
     215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta gac taa     1052
Val Leu Arg Val Asp Glu Ile Lys Pro Asp Val Ala Leu Leu Asp
             265                 270                 275
```

```
<210> SEQ ID NO 39
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ccugcucagu acuagaggaa ccgcagg                                              27

<210> SEQ ID NO 40
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cacgcagaaa gcgucuagcc auggcguuag uaugagug                                  38

<210> SEQ ID NO 41
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gccgaguagu guugggucgc gaaaggc                                              27

<210> SEQ ID NO 42
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cacgcagaaa gcgucuagcc auggcguuag uugagug                                   37

<210> SEQ ID NO 43
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gccgagugug uugggucgcg aaaggc                                               26
```

METHOD OF TREATING HEPATITIS C VIRUS

STATEMENT REGARDING FEDERALLY SPONSORED RESEARCH

The development of this invention was supported by National Institutes of Health grant 5 R03 A1057805-02. Thus, the Government may have rights in the invention.

SEQUENCE LISTING

The instant application contains a Sequence Listing which has been submitted via EFS-Web and is hereby incorporated by reference in its entirety. Said ASCII copy, created on Jan. 11, 2010, is named OCIRS330.txt, and is 82,006 bytes in size.

CROSS-REFERENCE TO RELATED APPLICATIONS

The present application is a national phase entry under 35 U.S.C. §371 of International Application No. PCT/US2008/000684 filed Jan. 18, 2008, published in English which claims priority from U.S. Provisional Patent Application No. 60/881,365 filed Jan. 19, 2007, all of which are incorporated herein by reference.

BACKGROUND OF THE INVENTION

Hepatitis C virus (HCV) is the major cause of chronic hepatitis, which can result in life threatening cirrhosis and hepatocellular carcinoma Saito, et al., Proc. Natl. Acad. Sci. USA 87:6547-6549 (1990). HCV is mainly transmitted parenterally or percutaneously. Non-parenteral exposure to HCV includes sexual activity, household contact and perinatal exposure. Presently, several drugs are used in the treatment of chronic hepatitis. Interferon (IFN)-α and IFN-β are the only approved therapeutic antiviral agents for chronic HCV infection. Hoofnagle, Adv. Intern. Med. 39:241-275 (1994). Administration of IFN-α may be in combination with ribavirin. Wang and Heinz, Prog. Drug Res. (Spec. No): 79-110 (2001).

Intensive efforts have continued towards the discovery of novel molecules or agents to treat this disease. For example, antisense molecules and catalytic ribozymes have been exploited for their antiviral activities. Wang and Heinze, supra.

SUMMARY OF THE INVENTION

A first aspect of the present invention is directed to a method for treating the Hepatitis C virus (HCV) infection comprising administering to a human in need thereof an effective amount of a pokeweed antiviral protein (PAP) mutant that is non-cytotoxic and which binds HCV IRES and inhibits translation of HCV RNA.

A second aspect of the present invention is directed to a method of inhibiting HCV IRES activity, comprising contacting human cells infected with HCV with an effective amount of a PAP mutant which is non-cytotoxic and binds HCV IRES and inhibits translation of HCV RNA.

A third aspect of the present invention is directed to various non-cytotoxic PAP mutants, per se. Nucleic acids encoding the mutants are also provided.

Applicants have discovered that some PAP mutants bind HCV IRES and thus inhibit translation of HCV RNA. Thus, propagation of the virus in the infected cell and infection of other cells are inhibited. Applicants also discovered that not all nontoxic PAP mutants bind HCV IRES and therefore do not inhibit translation of HCV RNA.

Applicants also discovered that other ribosome binding proteins (RIPS) do not bind HCV IRES and thus would not be suitable drug candidates for HCV treatment.

A further aspect of the present invention is directed to a non-cytotoxic PAP mutant that binds HCV IRES and inhibits translation of HCV RNA, conjugated to a hepatocyte receptor-specific ligand.

BRIEF DESCRIPTION OF THE DRAWINGS

FIG. 3 is a table showing cytotoxicity and depurination of PAP mutants in yeast cells after induction of PAP expression with galactose.

FIG. 6 is a graph showing cell viability of cells expressing PAP mutants. L251* (SEQ ID NO: 2); L252* (SEQ ID NO: 3); N253 (SEQ ID NO: 4); Y254 (SEQ ID NO: 5); T262 (SEQ ID NO: 6); Wt-PAP (SEQ ID NO: 7); V73E (SEQ ID NO: 8); G75D (SEQ ID NO: 9); C259A (SEQ ID NO: 10); L252K (SEQ ID NO: 11); N253A (SEQ ID NO: 12); N253R (SEQ ID NO: 13); L252K-N253A (SEQ ID NO:14); Y254* (SEQ ID NO: 15); N253A-Y254* (SEQ ID NO: 16) N253R-Y254* (SEQ ID NO: 17); N253D-Y254 SEQ ID NO: 18).

DETAILED DESCRIPTION

HCV is a member of the Flaviviridae family. Choo, et al., Science 244:359-362 (1989); Hijikata, et al., Proc. Natl. Acad. Sci. USA 88:5547-5551 (1991); Grakoui, et al., J. Virol. 67:1385-1395 (1993); Bartenschlager, et al., J. Virol. 68:5054-5055 (1994). The genome of the HCV virion genome contains a single-stranded positive sense RNA of about 9500 nucleotides (nt). It is composed of a long 5' untranslated region (UTR) of 341 nt, a single long open reading frame and a 3' UTR of about 240 nt. HCV does not possess a cap structure (7-methyl guanosine, or m$^7$Gppp) at the 5' end of its genome or a poly (A) tail at its 3' end. The 5' UTR of HCV RNA forms a highly structured internal ribosome entry site (IRES) (nt 40-370), which directs translation in a cap-independent manner. Wang, et al., J. Virol. 67:3338-3344 (1993).

Figure 1:
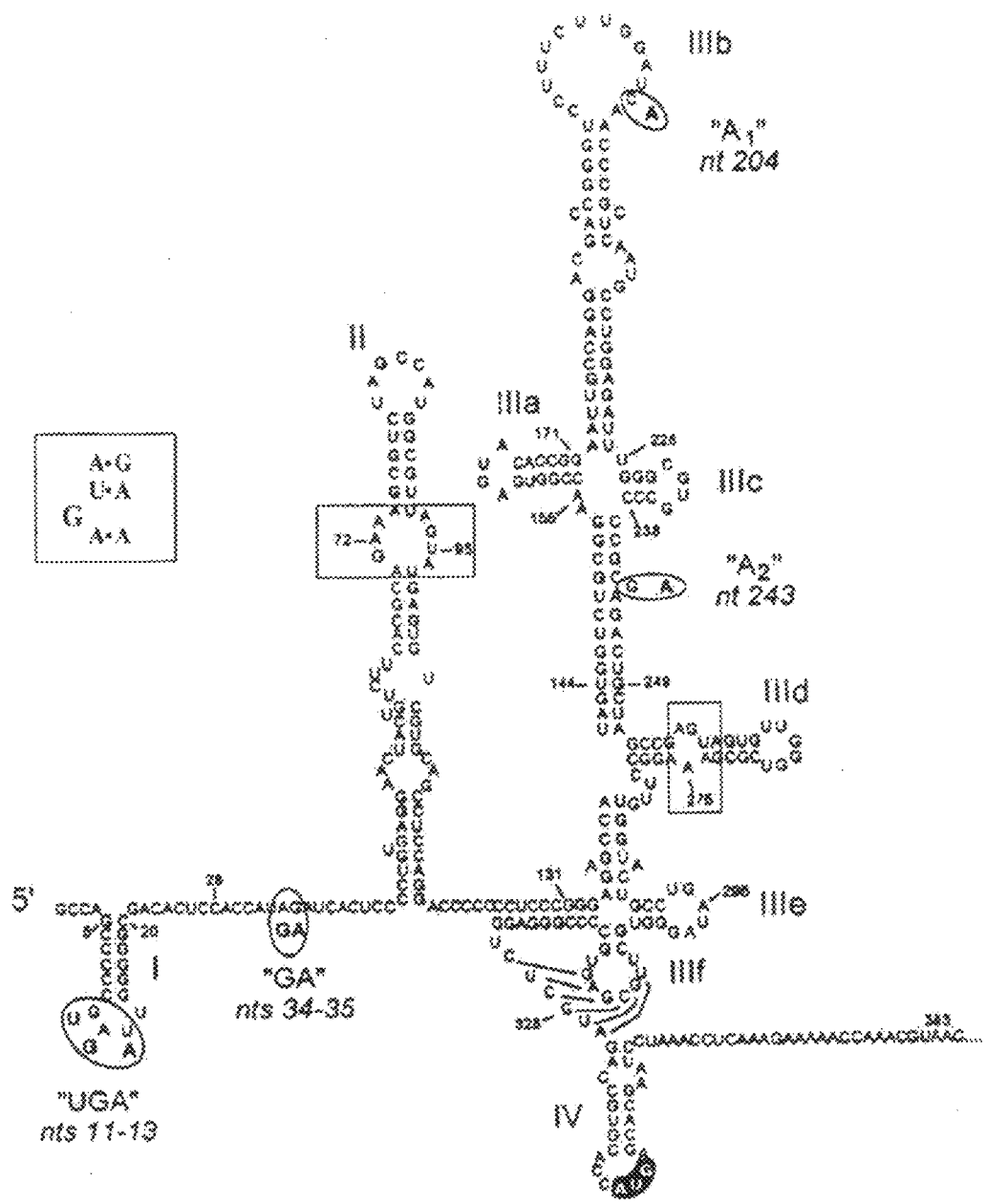
FIG. 1 is a schematic diagram showing tertiary structure and RNA sequence of the HCV IRES motif (SEQ ID NO: 1). The sequences that are similar to the α-sarcin ricin loop (SRL) in the stem loop II (SLII) and the stem loop IIId (SLIIId) are boxed and corresponding sequence is shown.

As illustrated in FIG. 1, the current structural model of HCV IRES indicates the presence of four major stem-loop domains and a pseudoknot. Brown, et al., Nucleic Acids Res. 20:5041-5045 (1992); Honda, et al., RNA 2:955-968 (1996); and Wang, et al., RNA 1:526-537 (1995). The structure of HCV IRES RNA bound to 40S ribosomal subunit was solved by cryo-electron microscopy and (cryo-EM) indicates that the IRES RNA binds to the head and platform of the 40S subunit in a single extended conformation. Spahn, et al., Science 291:1959 (2001). Stem-loop II of the HCV IRES RNA contacts the 40S subunit and is important for full IRES activity, but contributes little to binding affinity. Kieft, et al., RNA 7:194-206 (2001).

The structures of stem-loops IIId and IIIe have been solved by NMR spectroscopy. Klinck, et al, RNA 6:1423-1431 (2000); Lukaysky, et al., Nat. Struct. Biol. 7:1105-1110 (2000). Stem-loop IIId contains an internal asymmetric E-loop motif that is also present in the α-sarcin ricin loop (SRL) of the 28S rRNA. Correll et al., Proc. Natl. Acad. Sci. 95:13436-13441 (1998); Seggerson and Moore, RNA 4:1203-1215 (1998) (FIG. 1). Another SRL motif is also present on stem-loop II of the HCV IRES (FIG. 1).

SRL motif is defined as an asymmetric internal loop and is present in both the large subunit of rRNA and the loop E region of eukaryotic 5S rRNA. Leontis and Westhof, J. Mol. Biol. 283:571-583 (1998). It is characterized by a series of non-Watson-Crick base pairs (FIG. 1). Rijnbrand, et al., Virology 226:47-56 (1996) have shown that a mutation of A96G, disrupts the predicted SRL motif and significantly abrogates HCV IRES activity.

Pokeweed antiviral protein (PAP) is a 29-kDa protein isolated from pokeweed plants. It is synthesized in pokeweed plants as a 313-amino acid precursor and is processed to yield a mature or wild-type 262-amino acid (1-262) protein. See U.S. Pat. Nos. 5,756,322 and 5,880,329.

PAP is a ribosome inactivating protein (RIP). RIPs like PAP, such as ricin, Shiga toxin and Shiga-like toxin, catalytically inactivate ribosomes by catalytically removing an adenine (A4324) residue from the highly conserved sarcin/ricing loop (SRL) of the large rRNA. This depurination event of the SRL prevents eukaryotic translation initiation and serves to block protein synthesis.

By "wild-type PAP", it is meant the mature PAP amino acid sequence 1-262, excluding the 22-amino acid N-terminal signal peptide ("the N-terminal signal sequence of wild-type PAP"), and the 29 amino acid C-terminal extension (amino acids enumerated 263-291), set forth below. Thus, by the term "wild-type", or "mature PAP", it is meant the PAP amino acid sequence 1-262 (hereinafter PAP (1-262)). The following is the DNA (SEQ ID NO: 19) and corresponding amino acid sequence (SEQ ID NO: 20) of wild-type PAP, along with the N-terminal and C-terminal extensions:

```
5'-ATG AAG TCG ATG CTT GTG GTG ACA ATA TCA ATA
   Met Lys Ser Met Leu Val Val Thr Ile Ser Ile

TGG CTC ATT CTT GCA CCA ACT TCA ACT TGG GCT GTG AAT ACA ATC
   ATC TAC
   Trp Leu Ile Leu Ala Pro Thr Ser Thr Trp Ala (1) Val Asn Thr
   Ile Ile Tyr

AAT GTT GGA AGT ACC ACC ATT AGC AAA TAC GCC ACT TTT CTG AAT
   GAT CTT
   Asn Val Gly (10) Ser Thr Thr Ile Ser Lys Tyr Ala Thr Phe (20)
   Leu Asn Asp Leu

CGT AAT GAA GCG AAA GAT CCA AGT TTA AAA TGC TAT GGA ATA CCA
   ATG CTG Arg Asn
   Glu Ala Lys Asp (30) Pro Ser Leu Lys Cys Tyr Gly Ile Pro Met
   (40) Leu

CCC AAT ACA AAT ACA AAT CCA AAG TAC GTG TTG GTT GAG CTC CAA
   GGT TCA
   Pro Asn Thr Asn Thr Asn Pro Lys Tyr (50) Val Leu Val Glu Leu
   Gln Gly Ser

AAT AAA AAA ACC ATC ACA CTA ATG CTG AGA CGA AAC AAT TTG TAT
   GTG ATG
   Asn Lys (60) Lys Thr Ile Thr Leu Met Leu Arg Arg Asn (70) Asn
   Leu Tyr Val Met

GGT TAT TCT GAT CCC TTT GAA ACC AAT AAA TGT CGT TAC CAT ATC
   TTT AAT
   Gly Tyr Ser Asp Pro (80) Phe Glu Thr Asn Lys Cys Arg Tyr His
   Ile (90) Phe Asn
```

-continued

```
GAT ATC TCA GGT ACT GAA CGC CAA GAT GTA GAG ACT ACT CTT TGC
CCA AAT
Asp Ile Ser Gly Thr Glu Arg Gln (100) Asp Val Glu Thr Thr Leu
Cys Pro Asn
GCC AAT TCT CGT GTT ACT AAA AAC ATA AAC TTT GAT AGT CGA TAT
CCA ACA
Ala (110) Asn Ser Arg Val Ser Lys Asn Ile Asn Phe (120) Asp
Ser Arg Tyr Pro Thr
TTG GAA TCA AAA GCG GGA GTA AAA TCA AGA AGT CAG GTC CAA CTG
GGA ATT
Leu Glu Ser Lys (130) Ala Gly Val Lys Ser Arg Ser Gln Val Gln
(140) Leu Gly Ile
CAA ATA CTC GAC AGT AAT ATT GGA AAG ATT TCT GGA GTG ATG TCA
TTC ACT
Gln Ile Leu Asp Ser Asn Ile (150) Gly Lys Ile Ser Gly Val Met
Ser Phe Thr
GAG AAA ACC GAA GCC GAA TTC CTA TTG GTA GCC ATA CAA ATG GTA
TCA GAG
(160) Glu Lys Thr Glu Ala Glu Phe Leu Leu Val (170) Ala Ile
Gln Met Val Ser Glu
GCA GCA AGA TTC AAG TAC ATA GAG AAT CAG GTG AAA ACT AAT TTT
AAC AGA
Ala Ala Arg (180) Phe Lys Tyr Ile Glu Asn Gln Val Lys Thr
(190) Asn Phe Asn Arg
GCA TTC AAC CCT AAT CCC AAA GTA CTT AAT TTG CAA GAG AGA TGG
GGT AAG
Ala Phe Asn Pro Asn Pro (200) Lys Val Leu Asn Leu Gln Glu Thr
Trp Gly (210) Lys
ATT TCA ACA GCA ATT CAT GAT GCC AAG AAT GGA GTT TTA CCC AAA
CCT CTC
Ile Ser Thr Ala Ile His Asp Ala Lys (220) Asn Gly Val Leu Pro
Lys Pro Leu
GAG CTA GTG GAT GCC AGT GGT GCC AAG TGG ATA GTG TTG AGA GTG
GAT GAA
Glu Leu (230) Val Asp Ala Ser Gly Ala Lys Trp Ile Val (240)
Leu Arg Val Asp Glu
ATC AAG CCT GAT GTA GCA CTC TTA AAC TAC GTT GGT GGG AGC TGT
CAG ACA
Ile Lys Pro Asp Val (250) Ala Leu Leu Asn Tyr Val Gly Gly Ser
Cys (260) Gln (261) Thr
```

-continued

```
ACT TAT AAC CAA AAT GCC ATG TTT CCT CAA CTT ATA ATG TCT ACT

TAT TAT (262) Thr Tyr Asn Gln Asn Ala Met Phe (270) Pro Gln Leu Ile

Met Ser Thr Tyr Tyr (270) AAT TAC ATG GTT AAT CTT GGT GAT CTA TTT GAA GGA TTC

TGA-3'

Asn (280) Tyr Met Val Asn Leu Gly Asp Leu Phe Glu Gly (291)Phe
```

The nucleotide sequence further contains 5' and 3' non-coding, flanking sequences. Upon expression in eukaryotic cells, the N-terminal 22-amino acid sequence of wild-type PAP is co-translationally cleaved, yielding a polypeptide having a molecular weight of about 32 kD, which is then further processed by the cleavage of the C-terminal 29-amino acids ("the C-terminal extension of wild-type PAP" or "PAP (263-292)"), yielding wild-type, mature PAP or PAP (1-262) (i.e., that which is isolated from *Phytolacca americana* leaves), having a molecular weight of about 29 kD. See Irvin, et al., Pharmac. Ther. 55:279-302 (1992); Dore, et al., Nuc. Acids Res. 21(18):4200-05 (1993); Monzingo, et al., J. Mol. Biol. 233:705-15 (1993); and Turner. et al., Proc. Natl. Acad. Sci. USA 92:8448-52 (1995). PAP (1-262) has been further characterized in terms of three distinct domains, namely the N-terminal domain which includes amino acid residues 1-69, a central domain which includes amino acid residues 70-179 and a C-terminal domain which includes amino acid residues 180-262.

The PAP mutants embraced by the present invention include N-terminal domain mutants, central domain mutants and C-terminal domain mutants. The PAP mutants described herein are based upon mature wild-type PAP i.e., PAP (1-262). The specific mutants disclosed herein are described in terms of position in which the amino acid differs from PAP (1-262). For ease of understanding, they are described using the one-letter abbreviations of the respective amino acid as set forth in the following table.

TABLE I

| | |
|---|---|
| Alanine | A |
| Arginine | R |
| Asparagine | M |
| Aspartic Acid | D |
| Cysteine | C |
| Glutamine | Q |
| Glutamic Acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

In some embodiments, the PAP mutants differ from wild-type, mature PAP exclusively or substantially in that they contain one or more (e.g., two or three) amino acid substitutions at any of positions 1-262, which substitutions are typically conservative in nature. In other embodiments, the mutants are fragments of wild-type, mature PAP in that one or more amino acid residues are deleted from the N-terminus and/or C-terminus. In yet other embodiments, the PAP mutants are fragments of wild-type PAP and which also contain one or more (e.g., two or three) amino acid substitutions at any of positions 1-262, which substitutions are typically conservative in nature. More generally, PAP mutants differ from wild-type PAP in terms of one or more amino acid substitutions, deletions or additions.

The PAP mutants of the present invention are "non-cytotoxic," which as used herein means that they are less cytotoxic than wild-type PAP. The PAP mutants useful in the present invention typically do not significantly inhibit cell growth (like wild-type PAP) but in any event, they do not significantly affect cell viability. This determination can be made in accordance with a combination of standard techniques, illustrations of which are set forth United States Patent Application Publication 2004/0241673, which is hereby incorporated herein by reference.

A determination is made as to whether the PAP mutant inhibits cell growth as compared to wild type PAP, such as by growing cells such as yeast that produce the PAP mutant in question and plating and re-plating the cells on selective media. Another method involves measuring doubling time of growth of the cells in selective media after the induction of PAP production. PAP mutants exhibiting doubling times approximating the doubling time for wild-type PAP are considered toxic and thus outside the scope of the present invention. For example, in experiments conducted with *Saccharomyces cerevisiae* strain W303 cells, the doubling time for wild-type PAP was 10.4 hours. Hudak, et. al. Nuc. A Res. 32:4244-56 (2004). On the other hand, PAP mutants that caused doubling times of cells approximating the doubling time for PAPx (the active site mutant, PAP(1-262, E176V), tend to be noncytotoxic.

Figure 6:
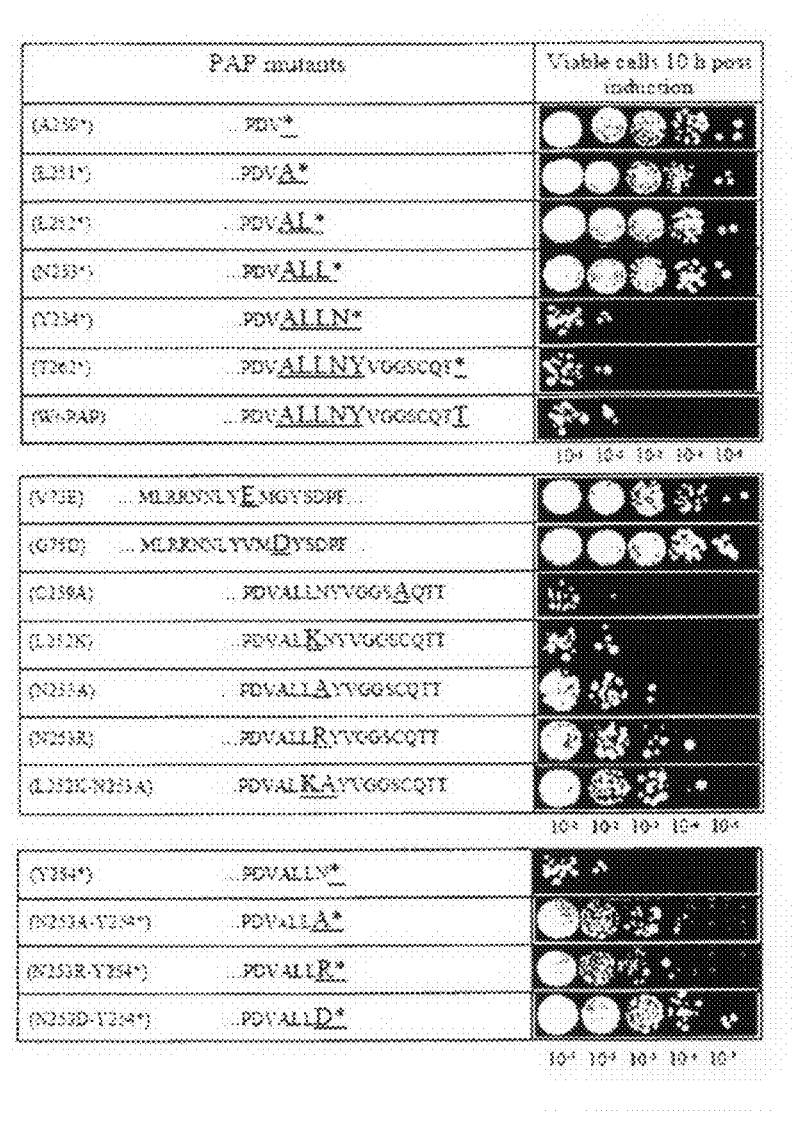

A determination is also made as to whether the PAP mutant causes cell death. In this case, a viability assay will distinguish between PAP mutants that cause cell death and that are toxic versus PAP mutants that might appear to be toxic (on account of having a doubling time approximately that for wild type PAP) but actually do not cause cell death, and thus are considered to be non-cytotoxic. There are also unusual situations in which a PAP mutant appears to be non-cytotoxic based on its effect on cell growth but is still toxic. Inhibition of cell growth does not always correlate with cell viability. Thus, regardless of whether one or more PAP mutants of the present invention have a significant effect on doubling time of cells, their effect on cell viability is less than that of wild-type PAP. FIG. 6 shows cell viability of select PAP mutants compared to wild-type PAP.

Without intending to be bound by any particular theory of operation, it is believed that inhibition of translation of HCV RNA occurs as a result of binding of a PAP mutant to the SRL motifs in stem-loop (SL) II or IIId of HCV IRES. Binding of PAP prevents interaction of the HCV IRES with the 40S ribosomal subunit and initiation of translation. Example 1 below details procedures for testing whether any given PAP mutant inhibits HCV IRES-directed translation. A determination as to whether a non-cytotoxic mutant binds HCV IRES can be made in accordance with standard techniques such as the protocol described in example 2 below.

Non-cytotoxic PAP mutants that bind HCV IRES and inhibit HCV RNA translation that may be used in the methods of the present invention for treatment of HCV include PAP (1-262, N70A), PAP(1-262, L71R), PAP(1-262, V73E), PAP (1-262, G75D), PAP(1-262, Y123A) and PAP(1-262, E176V).

As shown in FIG. 6, the C-terminally truncated Y254* mutant is toxic. Also shown is the reduction in cytotoxicity of PAP(1-262, N253A-Y254*) and PAP(1-262, N253R-Y254*) compared to the PAP(1-262, Y254*) mutant on its own. Substitution of aspartic acid for asparagine 253 in PAP(1-262, N253D-Y254*) also showed an even greater reduction in cytotoxicity (FIG. 6).

Accordingly, other PAP mutants that may be used in the methods of the present invention include PAP(1-262, N253A), PAP(1-262, N253R), PAP(1-262, L252K-N253A), PAP(1-262, N253A-Y254*), PAP(1-262, N253R-Y254*) and PAP(1-262, N253D-Y254*) where the '*' signifies a stop codon. Amino acid sequences of each of these six PAP mutants are as follows. Nucleic acids encoding PAP(1-262, N253A), PAP(1-262, N253R), PAP(1-262, L252K-N253A), PAP(1-262, N253A-Y254*), PAP(1-262, N253R-Y254*) and PAP(1-262, N253D-Y254*) are also described herein.

One subclass of PAP mutants believed to be useful for the purposes of this invention includes those mutants that are non-toxic, non-depurinating or non-toxic but less depurinating with respect to eukaryotic ribosomes but still capable of inhibiting HCV IRES. Examples of PAP mutants that are non-toxic and non-depurinating that are useful for the purposes of this invention are PAP(1-262, G75D) and PAP(1-262, E167V). Examples of PAP mutants that are non-toxic and less depurinating that are useful for the purposes of this invention are PAP(1-262, Y72A) and PAP(1-262, Y123A). Other examples that may be useful for purposes of this invention are PAP(1-262, A250*), PAP(1-262, L251*), PAP(1-262, L252*), PAP(1-262, N235A-Y254*), PAP(1-262, N253R-Y254*), and PAP(1-262, N253D-Y254*).

PAP(1-262, N253A) has a DNA (SEQ ID NO: 21) and amino acid sequence (SEQ ID NO: 22) of:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAAGAAAGTTGTGAGTT

AACTACAGGGCGAAAGTATTGGAACTAGCTAGTAGGAAGGGAAGATGAAGTCGATGCTTG

M K S M L V

TGGTGACAATATCAATATGGCTCATTCTTGCACCAACTTCAACTTGGGCTGTGAATACAA

V T I S I W L I L A P T S T W A V N T I

TCATCTACAATGTTGGAAGTACCACCATTAGCAAATACGCCACTTTTCTGAATGATCTTC

I Y N V G S T T I S K Y A T F L N D L R

GTAATGAAGCGAAAGATCCAAGTTTAAAATGCTATGGAATACCAATGCTGCCCAATACAA

N E A K D P S L K C Y G I P M L P N T N

ATACAAATCCAAAGTACGTGTTGGTTGAGCTCCAAGGTTCAAATAAAAAAACCATCACAC

T N P K Y V L V E L Q G S N K K T I T L

TAATGCTGAGACGAAACAATTTGTATGTGATGGGTTATTCTGATCCCTTTGAAACCAATA

M L R R N N L Y V M G Y S D P F E T N K

AATGTCGTTACCATATCTTTAATGATATCTCAGGTACTGAACGCCAAGATGTAGAGACTA

C R Y H I F N D I S G T E R Q D V E T T

CTCTTTGCCCAAATGCCAATTCTCGTGTTAGTAAAAACATAAACTTTGATAGTCGATATC

L C P N A N S R V S K N I N F D S R Y P

CAACATTGGAATCAAAAGCGGGAGTAAAATCAAGAAGTCAGGTCCAACTGGGAATTCAAA

T L E S K A G V K S R S Q V Q L G I Q I

TACTCGACAGTAATATTGGAAAGATTTCTGGAGTGATGTCATTCACTGAGAAAACCGAAG

L D S N I G K I S G V M S F T E K T E A

CCGAATTCCTATTGGTAGCCATACAAATGGTATCAGAGGCAGCAAGATTCAAGTACATAG

E F L L V A I Q M V S E A A R F K Y I E
```

```
AGAATCAGGTGAAAACTAATTTTAACAGAGCATTCAACCCTAATCCCAAAGTACTTAATT
 N  Q  V  K  T  N  F  N  R  A  F  N  P  N  P  K  V  L  N  L
TGCAAGAGACATGGGGTAAGATTTCAACAGCAATTCATGATGCCAAGAATGGAGTTTTAC
 Q  E  T  W  G  K  I  S  T  A  I  H  D  A  K  N  G  V  L  P
CCAAACCTCTCGAGCTAGTGGATGCCAGTGGTGCCAAGTGGATAGTGTTGAGAGTGGATG
 K  P  L  E  L  V  D  A  S  G  A  K  W  I  V  L  R  V  D  E
AAATCAAGCCTGATGTAGCACTCTTAGCCTACGTTGGTGGGAGCTGTCAGACAACTTATA
 I  K  P  D  V  A  L  L  A  Y  V  G  G  S  C  Q  T  T  Y  N
ACCAAAATGCCATGTTTCCTCAACTTATAATGTCTACTTATTATAATTACATGGTTAATC
 Q  N  A  M  F  P  Q  L  I  M  S  T  Y  Y  N  Y  M  V  N  L
TTGGTGATCTATTTGAAGGATTCTGATCATAAACATAATAAGGAGTATATATATATTACT
 G  D  L  F  E  G  F  *
CCAACTATATTATAAAGCTTAAATAAGAGGCCGTGTTAATTAGTACTTGTTGCCTTTTGC
TTTATGGTGTTGTTTATTATGCCTTGTATGCTTGTAATATTATCTAGAGAACAAGATGTA
CTGTGTAATAGTCTTGTTTGAAATAAAACTTCCAATTATGATGCAAAAAAAAAAAAAAA
```

Another nucleic acid (SEQ ID NO: 23) encoding PAP(1-262, N253A) (SEQ ID NO: 22) has the following sequence:

```
CTATGAAGTCGGGTCAAAGCATATACAGGCTATGCATTGTTAGAAACATTGATGCCTCTG
ATCCCGATAAACAATACAAATTAGACAATAAGATGACATACAAGTACCTAAACTGTGTAT
GGGGGAGTGAAACCTCAGCTGCTAAAAAAACGTTGTAAGAAAAAAGAAAGTTGTGAGTT
AACTACAGGGCGAAAGTATTGGAACTAGCTAGTAGGAAGGGAAGATGAAGTCGATGCTTG
 M  K  S  M  L  V
TGGTGACAATATCAATATGGCTCATTCTTGCACCAACTTCAACTTGGGCTGTGAATACAA
 V  T  I  S  I  W  L  I  L  A  P  T  S  T  W  A  V  N  T  I
TCATCTACAATGTTGGAAGTACCACCATTAGCAAATACGCCACTTTTCTGAATGATCTTC
 I  Y  N  V  G  S  T  T  I  S  K  Y  A  T  F  L  N  D  L  R
GTAATGAAGCGAAAGATCCAAGTTTAAAATGCTATGGAATACCAATGCTGCCCAATACAA
 N  E  A  K  D  P  S  L  K  C  Y  G  I  P  M  L  P  N  T  N
ATACAAATCCAAAGTACGTGTTGGTTGAGCTCCAAGGTTCAAATAAAAAAAACCATCACAC
 T  N  P  K  Y  V  L  V  E  L  Q  G  S  N  K  K  T  I  T  L
TAATGCTGAGACGAAACAATTTGTATGTGATGGGTTATTCTGATCCCTTTGAAACCAATA
 M  L  R  R  N  N  L  Y  V  M  G  Y  S  D  P  F  E  T  N  K
AATGTCGTTACCATATCTTTAATGATATCTCAGGTACTGAACGCCAAGATGTAGAGACTA
 C  R  Y  H  I  F  N  D  I  S  G  T  E  R  Q  D  V  E  T  T
CTCTTTGCCCAAATGCCAATTCTCGTGTTAGTAAAAACATAAACTTTGATAGTCGATATC
 L  C  P  N  A  N  S  R  V  S  K  N  I  N  F  D  S  R  Y  P
CAACATTGGAATCAAAAGCGGGAGTAAAATCAAGAAGTCAGGTCCAACTGGGAATTCAAA
 T  L  E  S  K  A  G  V  K  S  R  Q  V  Q  L  G  I  Q  I
TACTCGACAGTAATATTGGAAAGATTTCTGGAGTGATGTCATTCACTGAGAAACCGAAG
 L  D  S  N  I  G  K  I  S  G  V  M  S  F  T  E  K  T  E  A
```

```
CCGAATTCCTATTGGTAGCCATACAAATGGTATCAGAGGCAGCAAGATTCAAGTACATAG

E  F  L  L  V  A  I  Q  M  V  S  E  A  A  R  F  K  Y  I  E

AGAATCAGGTGAAAACTAATTTTAACAGAGCATTCAACCCTAATCCCAAAGTACTTAATT

N  Q  V  K  T  N  F  N  R  A  F  N  P  N  P  K  V  L  N  L

TGCAAGAGACATGGGGTAAGATTTCAACAGCAATTCATGATGCCAAGAATGGAGTTTTAC

Q  E  T  W  G  K  I  S  T  A  I  H  D  A  K  N  G  V  L  P

CCAAACCTCTCGAGCTAGTGGATGCCAGTGGTGCCAAGTGGATAGTGTTGAGAGTGGATG

K  P  L  E  L  V  D  A  S  G  A  K  W  I  V  L  R  V  D  E

AAATCAAGCCTGATGTAGCACTCTTAGCATACGTTGGTGGGAGCTGTCAGACAACTTATA

I  K  P  D  V  A  L  L  A  Y  V  G  G  S  C  Q  T  T  Y  N

ACCAAAATGCCATGTTTCCTCAACTTATAATGTCTACTTATTATAATTACATGGTTAATC

Q  N  A  M  F  P  Q  L  I  M  S  T  Y  Y  N  Y  M  V  N  L

TTGGTGATCTATTTGAAGGATTCTGATCATAAACATAATAAGGAGTATATATATATTACT

G  D  L  F  E  G  F  *

CCAACTATATTATAAAGCTTAAATAAGAGGCCGTGTTAATTAGTACTTGTTGCCTTTTGC

TTTATGGTGTTGTTTATTATGCCTTGTATGCTTGTAATATTATCTAGAGAACAAGATGTA

CTGTGTAATAGTCTTGTTTGAAATAAAACTTCCAATTATGATGCAAAAAAAAAAAAAAA
```

PAP(1-262, N253R) has a DNA (SEQ ID NO: 24) and amino acid sequence (SEQ ID NO: 25) of:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAGAAAGTTGTGAGTT

AACTACAGGGCGAAAGTATTGGAACTAGCTAGTAGGAAGGGAAGATGAAGTCGATGCTTG

M  K  S  M  L  V

TGGTGACAATATCAATATGGCTCATTCTTGCACCAACTTCAACTTGGGCTGTGAATACAA

V  T  I  S  I  W  L  I  L  A  P  T  S  T  W  A  V  N  T  I

TCATCTACAATGTTGGAAGTACCACCATTAGCAAATACGCCACTTTTCTGAATGATCTTC

I  Y  N  V  G  S  T  T  I  S  K  Y  A  T  F  L  N  D  L  R

GTAATGAAGCGAAAGATCCAAGTTTAAAATGCTATGGAATACCAATGCTGCCCAATACAA

N  E  A  K  D  P  S  L  K  C  Y  G  I  P  M  L  P  N  T  N

ATACAAATCCAAAGTACGTGTTGGTTGAGCTCCAAGGTTCAAATAAAAAAACCATCACAC

T  N  P  K  Y  V  L  V  E  L  Q  G  S  N  K  K  T  I  T  L

TAATGCTGAGACGAAACAATTTGTATGTGATGGGTTATTCTGATCCCTTTGAAACCAATA

M  L  R  R  N  N  L  Y  V  M  G  Y  S  D  P  F  E  T  N  K

AATGTCGTTACCATATCTTTAATGATATCTCAGGTACTGAACGCCAAGATGTAGAGACTA

C  R  Y  H  I  F  N  D  I  S  G  T  E  R  Q  D  V  E  T  T

CTCTTTGCCCAAATGCCAATTCTCGTGTTAGTAAAAACATAAACTTTGATAGTCGATATC

L  C  P  N  A  N  S  R  V  S  K  N  I  N  F  D  S  R  Y  P
```

CAACATTGGAATCAAAAGCGGGAGTAAAATCAAGAAGTCAGGTCCAACTGGGAATTCAAA

T L E S K A G V K S R S Q V Q L G I Q I

TACTCGACAGTAATATTGGAAAGATTTCTGGAGTGATGTCATTCACTGAGAAAACCGAAG

L D S N I G K I S G V M S F T E K T E A

CCGAATTCCTATTGGTAGCCATACAAATGGTATCAGAGGCAGCAAGATTCAAGTACATAG

E F L L V A I Q M V S E A A R F K Y I E

AGAATCAGGTGAAAACTAATTTTAACAGAGCATTCAACCCTAATCCCAAAGTACTTAATT

N Q V K T N F N R A F N P N P K V L N L

TGCAAGAGACATGGGGTAAGATTTCAACAGCAATTCATGATGCCAAGAATGGAGTTTTAC

Q E T W G K I S T A I H D A K N G V L P

CCAAACCTCTCGAGCTAGTGGATGCCAGTGGTGCCAAGTGGATAGTGTTGAGAGTGGATG

K P L E L V D A S G A K W I V L R V D E

AAATCAAGCCTGATGTAGCACTCTTA<u>AGA</u>TACGTTGGTGGGAGCTGTCAGACAACTTATA

I K P D V A L L R Y V G G S C Q T T Y N

ACCAAAATGCCATGTTTCCTCAACTTATAATGTCTACTTATTATAATTACATGGTTAATC

Q N A M F P Q L I M S T Y Y N Y M V N L

TTGGTGATCTATTTGAAGGATTCTGATCATAAACATAATAAGGAGTATATATATATTACT

G D L F E G F *

CCAACTATATTATAAAGCTTAAATAAGAGGCCGTGTTAATTAGTACTTGTTGCCTTTTGC

TTTATGGTGTTGTTTATTATGCCTTGTATGCTTGTAATATTATCTAGAGAACAAGATGTA

CTGTGTAATAGTCTTGTTTGAAATAAAACTTCCAATTATGATGCAAAAAAAAAAAAAAA

Another nucleic acid (SEQ ID NO: 26) encoding (1-262, N253R) (SEQ ID NO: 25) has the following sequence:

CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAAGAAAGTTGTGAGTT

AACTACAGGGCGAAAGTATTGGAACTAGCTAGTAGGAAGGGAAGATGAAGTCGATGCTTG

M K S M L V

TGGTGACAATATCAATATGGCTCATTCTTGCACCAACTTCAACTTGGGCTGTGAATACAA

V T I S I W L I L A P T S T W A V N T I

TCATCTACAATGTTGGAAGTACCACCATTAGCAAATACGCCACTTTTCTGAATGATCTTC

I Y N V G S T T I S K Y A T F L N D L R

GTAATGAAGCGAAAGATCCAAGTTTAAAATGCTATGGAATACCAATGCTGCCCAATACAA

N E A K D P S L K C Y G I P M L P N T N

ATACAAATCCAAAGTACGTGTTGGTTGAGCTCCAAGGTTCAAATAAAAAAACCATCACAC

T N P K Y V L V E L Q G S N K K T I T L

TAATGCTGAGACGAAACAATTTGTATGTGATGGGTTATTCTGATCCCTTTGAAACCAATA

M L R R N N L Y V M G Y S D P F E T N K

-continued

```
AATGTCGTTACCATATCTTTAATGATATCTCAGGTACTGAACGCCAAGATGTAGAGACTA

C R Y H I F N D I S G T E R Q D V E T T

CTCTTTGCCCAAATGCCAATTCTCGTGTTAGTAAAAACATAAACTTTGATAGTCGATATC

L C P N A N S R V S K N I N F D S R Y P

CAACATTGGAATCAAAAGCGGGAGTAAAATCAAGAAGTCAGGTCCAACTGGGAATTCAAA

T L E S K A G V K S R S Q V Q L G I Q I

TACTCGACAGTAATATTGGAAAGATTTCTGGAGTGATGTCATTCACTGAGAAAACCGAAG

L D S N I G K I S G V M S F T E K T E A

CCGAATTCCTATTGGTAGCCATACAAATGGTATCAGAGGCAGCAAGATTCAAGTACATAG

E F L L V A I Q M V S E A A R F K Y I E

AGAATCAGGTGAAAACTAATTTTAACAGAGCATTCAACCCTAATCCCAAAGTACTTAATT

N Q V K T N F N R A F N P N P K V L N L

TGCAAGAGACATGGGGTAAGATTTCAACAGCAATTCATGATGCCAAGAATGGAGTTTTAC

Q E T W G K I S T A I H D A K N G V L P

CCAAACCTCTCGAGCTAGTGGATGCCAGTGGTGCCAAGTGGATAGTGTTGAGAGTGGATG

K P L E L V D A S G A K W I V L R V D E

AAATCAAGCCTGATGTAGCACTCTTAAGGTACGTTGGTGGGAGCTGTCAGACAACTTATA

I K P D V A L L R Y V G G S C Q T T Y N

ACCAAAATGCCATGTTTCCTCAACTTATAATGTCTACTTATTATAATTACATGGTTAATC

Q N A M F P Q L I M S T Y Y N Y M V N L

TTGGTGATCTATTTGAAGGATTCTGATCATAAACATAATAAGGAGTATATATATATTACT

G D L F E G F *

CCAACTATATTATAAAGCTTAAATAAGAGGCCGTGTTAATTAGTACTTGTTGCCTTTTGC

TTTATGGTGTTGTTTATTATGCCTTGTATGCTTGTAATATTATCTAGAGAACAAGATGTA

CTGTGTAATAGTCTTGTTTGAAATAAAACTTCCAATTATGATGCAAAAAAAAAAAAAA
```

PAP(1-262, L252K-N253A) has a DNA and amino acid sequence of: PAP(1-262, L252K-N253A) has a DNA (SEQ ID NO: 27) and amino acid sequence (SEQ ID NO: 28) of:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAAGAAAGTTGTGAGTT

AACTACAGGGCGAAAGTATTGGAACTAGCTAGTAGGAAGGGAAGATGAAGTCGATGCTTG

M K S M L V

TGGTGACAATATCAATATGGCTCATTCTTGCACCAACTTCAACTTGGGCTGTGAATACAA

V T I S I W L I L A P T S T W A V N T I

TCATCTACAATGTTGGAAGTACCACCATTAGCAAATACGCCACTTTTCTGAATGATCTTC

I Y N V G S T T I S K Y A T F L N D L R

GTAATGAAGCGAAAGATCCAAGTTTAAAATGCTATGGAATACCAATGCTGCCCAATACAA

N E A K D P S L K C Y G I P M L P N T N
```

-continued

```
ATACAAATCCAAAGTACGTGTTGGTTGAGCTCCAAGGTTCAAATAAAAAAACCATCACAC
```
T N P K Y V L V E L Q G S N K K T I T L
```
TAATGCTGAGACGAAACAATTTGTATGTGATGGGTTATTCTGATCCCTTTGAAACCAATA
```
M L R R N N L Y V M G Y S D P F E T N K
```
AATGTCGTTACCATATCTTTAATGATATCTCAGGTACTGAACGCCAAGATGTAGAGACTA
```
C R Y H I F N D I S G T E R Q D V E T T
```
CTCTTTGCCCAAATGCCAATTCTCGTGTTAGTAAAAACATAAACTTTGATAGTCGATATC
```
L C P N A N S R V S K N I N F D S R Y P
```
CAACATTGGAATCAAAAGCGGGAGTAAAATCAAGAAGTCAGGTCCAACTGGGAATTCAAA
```
T L E S K A G V K S R S Q V Q L G I Q I
```
TACTCGACAGTAATATTGGAAAGATTTCTGGAGTGATGTCATTCACTGAGAAAACCGAAG
```
L D S N I G K I S G V M S F T E K T E A
```
CCGAATTCCTATTGGTAGCCATACAAATGGTATCAGAGGCAGCAAGATTCAAGTACATAG
```
E F L L V A I Q M V S E A A R F K Y I E
```
AGAATCAGGTGAAAACTAATTTTAACAGAGCATTCAACCCTAATCCCAAAGTACTTAATT
```
N Q V K T N F N R A F N P N P K V L N L
```
TGCAAGAGACATGGGGTAAGATTTCAACAGCAATTCATGATGCCAAGAATGGAGTTTTAC
```
Q E T W G K I S T A I H D A K N G V L P
```
CCAAACCTCTCGAGCTAGTGGATGCCAGTGGTGCCAAGTGGATAGTGTTGAGAGTGGATG
```
K P L E L V D A S G A K W I V L R V D E
```
AAATCAAGCCTGATGTAGCACTCAAGGCATACGTTGGTGGGAGCTGTCAGACAACTTATA
```
I K P D V A L K A Y V G G S C Q T T Y N
```
ACCAAAATGCCATGTTTCCTCAACTTATAATGTCTACTTATTATAATTACATGGTTAATC
```
Q N A M F P Q L I M S T Y Y N Y M V N L
```
TTGGTGATCTATTTGAAGGATTCTGATCATAAACATAATAAGGAGTATATATATATTACT
```
G D L F E G F *
```
CCAACTATATTATAAAGCTTAAATAAGAGGCCGTGTTAATTAGTACTTGTTGCCTTTTGC
TTTATGGTGTTGTTTATTATGCCTTGTATGCTTGTAATATTATCTAGAGAACAAGATGTA
CTGTGTAATAGTCTTGTTTGAAATAAAACTTCCAATTATGATGCAAAAAAAAAAAAAAA
```

Another nucleic acid (SEQ ID NO: 29) encoding PAP(1-262, L252K-N253A) (SEQ ID NO: 28) has the following sequence:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTATGG

GGGAGTGAAACCTCAGCTGCTAAAAAAACGTTGTAAGAAAAAAAGAAAGTTGTGAGTT

AACTACAGGGCGAAAGTATTGGAACTAGCTAGTAGGAAGGGAAGATGAAGTCGATGCTTG
```
M K S M L V
```
TGGTGACAATATCAATATGGCTCATTCTTGCACCAACTTCAACTTGGGCTGTGAATACAA
```
V T I S I W L I L A P T S T W A V N T I

-continued

```
TCATCTACAATGTTGGAAGTACCACCATTAGCAAATACGCCACTTTTCTGAATGATCTTC
 I  Y  N  V  G  S  T  T  I  S  K  Y  A  T  F  L  N  D  L  R

GTAATGAAGCGAAAGATCCAAGTTTAAAATGCTATGGAATACCAATGCTGCCCAATACAA
 N  E  A  K  D  P  S  L  K  C  Y  G  I  P  M  L  P  N  T  N

ATACAAATCCAAAGTACGTGTTGGTTGAGCTCCAAGGTTCAAATAAAAAACCATCACAC
 T  N  P  K  Y  V  L  V  E  L  Q  G  S  N  K  K  T  I  T  L

TAATGCTGAGACGAAACAATTTGTATGTGATGGGTTATTCTGATCCCTTTGAAACCAATA
 M  L  R  R  N  N  L  Y  V  M  G  Y  S  D  P  F  E  T  N  K

AATGTCGTTACCATATCTTTAATGATATCTCAGGTACTGAACGCCAAGATGTAGAGACTA
 C  R  Y  H  I  F  N  D  I  S  G  T  E  R  Q  D  V  E  T  T

CTCTTTGCCCAAATGCCAATTCTCGTGTTAGTAAAAACATAAACTTTGATAGTCGATATC
 L  C  P  N  A  N  S  R  V  S  K  N  I  N  F  D  S  R  Y  P

CAACATTGGAATCAAAAGCGGGAGTAAAATCAAGAAGTCAGGTCCAACTGGGAATTCAAA
 T  L  E  S  K  A  G  V  K  S  R  S  Q  V  Q  L  G  I  Q  I

TACTCGACAGTAATATTGGAAAGATTTCTGGAGTGATGTCATTCACTGAGAAACCGAAG
 L  D  S  N  I  G  K  I  S  G  V  M  S  F  T  E  K  T  E  A

CCGAATTCCTATTGGTAGCCATACAAATGGTATCAGAGGCAGCAAGATTCAAGTACATAG
 E  F  L  L  V  A  I  Q  M  V  S  E  A  A  R  F  K  Y  I  E

AGAATCAGGTGAAAACTAATTTTAACAGAGCATTCAACCCTAATCCCAAAGTACTTAATT
 N  Q  V  K  T  N  F  N  R  A  F  N  P  N  P  K  V  L  N  L

TGCAAGAGACATGGGGTAAGATTTCAACAGCAATTCATGATGCCAAGAATGGAGTTTTAC
 Q  E  T  W  G  K  I  S  T  A  I  H  D  A  K  N  G  V  L  P

CCAAACCTCTCGAGCTAGTGGATGCCAGTGGTGCCAAGTGGATAGTGTTGAGAGTGGATG
 K  P  L  E  L  V  D  A  S  G  A  K  W  I  V  L  R  V  D  E

AAATCAAGCCTGATGTAGCACTCAAAGCCTACGTTGGTGGGAGCTGTCAGGACAACTTATA
 I  K  P  D  V  A  L  K  A  Y  V  G  G  S  C  Q  T  T  Y  N

ACCAAAATGCCATGTTTCCTCAACTTATAATGTCTACTTATTATAATTACATGGTTAATC
 Q  N  A  M  F  P  Q  L  I  M  S  T  Y  Y  N  Y  M  V  N  L

TTGGTGATCTATTTGAAGGATTCTGATCATAAACATAATAAGGAGTATATATATATTACT
 G  D  L  F  E  G  F  *

CCAACTATATTATAAAGCTTAAATAAGAGGCCGTGTTAATTAGTACTTGTTGCCTTTTGC

TTTATGGTGTTGTTTATTATGCCTTGTATGCTTGTAATATTATCTAGAGAACAAGATGTA

CTGTGTAATAGTCTTGTTTGAAATAAAACTTCCAATTATGATGCAAAAAAAAAAAAAAA
```

55

PAP(1-262, N253A-Y254*) has a DNA (SEQ ID NO: 30) and amino acid sequence (SEQ ID NO: 31) of:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAGAAAGTTGTGAGTT
```

```
AACTACAGGGCGAAAGTATTGGAACTAGCTAGTAGGAAGGGAAGATGAAGTCGATGCTTG
 M  K  S  M  L  V
TGGTGACAATATCAATATGGCTCATTCTTGCACCAACTTCAACTTGGGCTGTGAATACAA
 V  T  I  S  I  W  L  I  L  A  P  T  S  T  W  A  V  N  T  I
TCATCTACAATGTTGGAAGTACCACCATTAGCAAATACGCCACTTTTCTGAATGATCTTC
 I  Y  N  V  G  S  T  T  I  S  K  Y  A  T  F  L  N  D  L  R
GTAATGAAGCGAAAGATCCAAGTTTAAAATGCTATGGAATACCAATGCTGCCCAATACAA
 N  E  A  K  D  P  S  L  K  C  Y  G  I  P  M  L  P  N  T  N
ATACAAATCCAAAGTACGTGTTGGTTGAGCTCCAAGGTTCAAATAAAAAACCATCACAC
 T  N  P  K  Y  V  L  V  E  L  Q  G  S  N  K  K  T  I  T  L
TAATGCTGAGACGAAACAATTTGTATGTGATGGGTTATTCTGATCCCTTTGAAACCAATA
 M  L  R  R  N  N  L  Y  V  M  G  Y  S  D  P  F  E  T  N  K
AATGTCGTTACCATATCTTTAATGATATCTCAGGTACTGAACGCCAAGATGTAGAGACTA
 C  R  Y  H  I  F  N  D  I  S  G  T  E  R  Q  D  V  E  T  T
CTCTTTGCCCAAATGCCAATTCTCGTGTTAGTAAAAACATAAACTTTGATAGTCGATATC
 L  C  P  N  A  N  S  R  V  S  K  N  I  N  F  D  S  R  Y  P
CAACATTGGAATCAAAAGCGGGAGTAAAATCAAGAAGTCAGGTCCAACTGGGAATTCAAA
 T  L  E  S  K  A  G  V  K  S  R  S  Q  V  Q  L  G  I  Q  I
TACTCGACAGTAATATTGGAAAGATTTCTGGAGTGATGTCATTCACTGAGAAAACCGAAG
 L  D  S  N  I  G  K  I  S  G  V  M  S  F  T  E  K  T  E  A
CCGAATTCCTATTGGTAGCCATACAAATGGTATCAGAGGCAGCAAGATTCAAGTACATAG
 E  F  L  L  V  A  I  Q  M  V  S  E  A  A  R  F  K  Y  I  E
AGAATCAGGTGAAAACTAATTTTAACAGAGCATTCAACCCTAATCCCAAAGTACTTAATT
 N  Q  V  K  T  N  F  N  R  A  F  N  P  N  P  K  V  L  N  L
TGCAAGAGACATGGGGTAAGATTTCAACAGCAATTCATGATGCCAAGAATGGAGTTTTAC
 Q  E  T  W  G  K  I  S  T  A  I  H  D  A  K  N  G  V  L  P
CCAAACCTCTCGAGCTAGTGGATGCCAGTGGTGCCAAGTGGATAGTGTTGAGAGTGGATG
 K  P  L  E  L  V  D  A  S  G  A  K  W  I  V  L  R  V  D  E
AAATCAAGCCTGATGTAGCACTCTTAGCCTAA
 I  K  P  D  V  A  L  L  A  *
```

Another nucleic acid (SEQ ID NO: 32) encoding PAP(1-262, N253A-Y254*) (SEQ ID NO: 31) has the following sequence:

```
CTATGAAGTCGGGTCAAAGCATATACAGGCTATGCATTGTTAGAAACATTGATGCCTCTG
ATCCCGATAAACAATACAAATTAGACAATAAGATGACATACAAGTACCTAAACTGTGTAT
GGGGGAGTGAAACCTCAGCTGCTAAAAAAACGTTGTAAGAAAAAAAGAAAGTTGTGAGTT
AACTACAGGGCGAAAGTATTGGAACTAGCTAGTAGGAAGGGAAGATGAAGTCGATGCTTG
 M  K  S  M  L  V
TGGTGACAATATCAATATGGCTCATTCTTGCACCAACTTCAACTTGGGCTGTGAATACAA
 V  T  I  S  I  W  L  I  L  A  P  T  S  T  W  A  V  N  T  I
```

```
TCATCTACAATGTTGGAAGTACCACCATTAGCAAATACGCCACTTTTCTGAATGATCTTC
 I  Y  N  V  G  S  T  T  I  S  K  Y  A  T  F  L  N  D  L  R

GTAATGAAGCGAAAGATCCAAGTTTAAAATGCTATGGAATACCAATGCTGCCCAATACAA
 N  E  A  K  D  P  S  L  K  C  Y  G  I  P  M  L  P  N  T  N

ATACAAATCCAAAGTACGTGTTGGTTGAGCTCCAAGGTTCAAATAAAAAACCATCACAC
 T  N  P  K  Y  V  L  V  E  L  Q  G  S  N  K  K  T  I  T  L

TAATGCTGAGACGAAACAATTTGTATGTGATGGGTTATTCTGATCCCTTTGAAACCAATA
 M  L  R  R  N  N  L  Y  V  M  G  Y  S  D  P  F  E  T  N  K

AATGTCGTTACCATATCTTTAATGATATCTCAGGTACTGAACGCCAAGATGTAGAGACTA
 C  R  Y  H  I  F  N  D  I  S  G  T  E  R  Q  D  V  E  T  T

CTCTTTGCCCAAATGCCAATTCTCGTGTTAGTAAAAACATAAACTTTGATAGTCGATATC
 L  C  P  N  A  N  S  R  V  S  K  N  I  N  F  D  S  R  Y  P

CAACATTGGAATCAAAAGCGGGAGTAAAATCAAGAAGTCAGGTCCAACTGGGAATTCAAA
 T  L  E  S  K  A  G  V  K  S  R  S  Q  V  Q  L  G  I  Q  I

TACTCGACAGTAATATTGGAAAGATTTCTGGAGTGATGTCATTCACTGAGAAAACCGAAG
 L  D  S  N  I  G  K  I  S  G  V  M  S  F  T  E  K  T  E  A

CCGAATTCCTATTGGTAGCCATACAAATGGTATCAGAGGCAGCAAGATTCAAGTACATAG
 E  F  L  L  V  A  I  Q  M  V  S  E  A  A  R  F  K  Y  I  E

AGAATCAGGTGAAAACTAATTTTAACAGAGCATTCAACCCTAATCCCAAAGTACTTAATT
 N  Q  V  K  T  N  F  N  R  A  F  N  P  N  P  K  V  L  N  L

TGCAAGAGACATGGGGTAAGATTTCAACAGCAATTCATGATGCCAAGAATGGAGTTTTAC
 Q  E  T  W  G  K  I  S  T  A  I  H  D  A  K  N  G  V  L  P

CCAAACCTCTCGAGCTAGTGGATGCCAGTGGTGCCAAGTGGATAGTGTTGAGAGTGGATG
 K  P  L  E  L  V  D  A  S  G  A  K  W  I  V  L  R  V  D  E

AAATCAAGCCTGATGTAGCACTCTTAGCATAA
 I  K  P  D  V  A  L  L  A  *
```

PAP(1-262, N253R-Y254*) has a DNA (SEQ ID NO: 33) and amino acid sequence (SEQ ID NO: 34) of:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAAGAAAGTTGTGAGTT

AACTACAGGGCGAAAGTATTGGAACTAGCTAGTAGGAAGGGAAGATGAAGTCGATGCTTG
                                                M  K  S  M  L  V

TGGTGACAATATCAATATGGCTCATTCTTGCACCAACTTCAACTTGGGCTGTGAATACAA
 V  T  I  S  I  W  L  I  L  A  P  T  S  T  W  A  V  N  T  I

TCATCTACAATGTTGGAAGTACCACCATTAGCAAATACGCCACTTTTCTGAATGATCTTC
 I  Y  N  V  G  S  T  T  I  S  K  Y  A  T  F  L  N  D  L  R

GTAATGAAGCGAAAGATCCAAGTTTAAAATGCTATGGAATACCAATGCTGCCCAATACAA
 N  E  A  K  D  P  S  L  K  C  Y  G  I  P  M  L  P  N  T  N
```

```
ATACAAATCCAAAGTACGTGTTGGTTGAGCTCCAAGGTTCAAATAAAAAAACCATCACAC

T  N  P  K  Y  V  L  V  E  L  Q  G  S  N  K  K  T  I  T  L

TAATGCTGAGACGAAACAATTTGTATGTGATGGGTTATTCTGATCCCTTTGAAACCAATA

M  L  R  R  N  N  L  Y  V  M  G  Y  S  D  P  F  E  T  N  K

AATGTCGTTACCATATCTTTAATGATATCTCAGGTACTGAACGCCAAGATGTAGAGACTA

C  R  Y  H  I  F  N  D  I  S  G  T  E  R  Q  D  V  E  T  T

CTCTTTGCCCAAATGCCAATTCTCGTGTTAGTAAAAACATAAACTTTGATAGTCGATATC

L  C  P  N  A  N  S  R  V  S  K  N  I  N  F  D  S  R  Y  P

CAACATTGGAATCAAAAGCGGGAGTAAAATCAAGAAGTCAGGTCCAACTGGGAATTCAAA

T  L  E  S  K  A  G  V  K  S  R  S  Q  V  Q  L  G  I  Q  I

TACTCGACAGTAATATTGGAAAGATTTCTGGAGTGATGTCATTCACTGAGAAAACCGAAG

L  D  S  N  I  G  K  I  S  G  V  M  S  F  T  E  K  T  E  A

CCGAATTCCTATTGGTAGCCATACAAATGGTATCAGAGGCAGCAAGATTCAAGTACATAG

E  F  L  L  V  A  I  Q  M  V  S  E  A  A  R  F  K  Y  I  E

AGAATCAGGTGAAAACTAATTTTAACAGAGCATTCAACCCTAATCCCAAAGTACTTAATT

N  Q  V  K  T  N  F  N  R  A  F  N  P  N  P  K  V  L  N  L

TGCAAGAGACATGGGGTAAGATTTCAACAGCAATTCATGATGCCAAGAATGGAGTTTTAC

Q  E  T  W  G  K  I  S  T  A  I  H  D  A  K  N  G  V  L  P

CCAAACCTCTCGAGCTAGTGGATGCCAGTGGTGCCAAGTGGATAGTGTTGAGAGTGGATG

K  P  L  E  L  V  D  A  S  G  A  K  W  I  V  L  R  V  D  E

AAATCAAGCCTGATGTAGCACTCTTAAGATAA

I  K  P  D  V  A  L  L  R  *
```

Another nucleic acid (SEQ ID NO: 35) encoding PAP(1-262, N253R-Y254*) (SEQ ID NO: 34) has the following sequence:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAAGAAAGTTGTGAGTT

AACTACAGGGCGAAAGTATTGGAACTAGCTAGTAGGAAGGGAAGATGAAGTCGATGCTTG

M  K  S  M  L  V

TGGTGACAATATCAATATGGCTCATTCTTGCACCAACTTCAACTTGGGCTGTGAATACAA

V  T  I  S  I  W  L  I  L  A  P  T  S  T  W  A  V  N  T  I

TCATCTACAATGTTGGAAGTACCACCATTAGCAAATACGCCACTTTTCTGAATGATCTTC

I  Y  N  V  G  S  T  T  I  S  K  Y  A  T  F  L  N  D  L  R

GTAATGAAGCGAAAGATCCAAGTTTAAAATGCTATGGAATACCAATGCTGCCCAATACAA

N  E  A  K  D  P  S  L  K  C  Y  G  I  P  M  L  P  N  T  N

ATACAAATCCAAAGTACGTGTTGGTTGAGCTCCAAGGTTCAAATAAAAAAACCATCACAC

T  N  P  K  Y  V  L  V  E  L  Q  G  S  N  K  K  T  I  T  L

TAATGCTGAGACGAAACAATTTGTATGTGATGGGTTATTCTGATCCCTTTGAAACCAATA

M  L  R  R  N  N  L  Y  V  M  G  Y  S  D  P  F  E  T  N  K
```

-continued

```
AATGTCGTTACCATATCTTTAATGATATCTCAGGTACTGAACGCCAAGATGTAGAGACTA
```
C R Y H I F N D I S G T E R Q D V E T T
```
CTCTTTGCCCAAATGCCAATTCTCGTGTTAGTAAAAACATAAACTTTGATAGTCGATATC
```
L C P N A N S R V S K N I N F D S R Y P
```
CAACATTGGAATCAAAAGCGGGAGTAAAATCAAGAAGTCAGGTCCAACTGGGAATTCAAA
```
T L E S K A G V K S R S Q V Q L G I Q I
```
TACTCGACAGTAATATTGGAAAGATTTCTGGAGTGATGTCATTCACTGAGAAAACCGAAG
```
L D S N I G K I S G V M S F T E K T E A
```
CCGAATTCCTATTGGTAGCCATACAAATGGTATCAGAGGCAGCAAGATTCAAGTACATAG
```
E F L L V A I Q M V S E A A R F K Y I E
```
AGAATCAGGTGAAAACTAATTTTAACAGAGCATTCAACCCTAATCCCAAAGTACTTAATT
```
N Q V K T N F N R A F N P N P K V L N L
```
TGCAAGAGACATGGGGTAAGATTTCAACAGCAATTCATGATGCCAAGAATGGAGTTTTAC
```
Q E T W G K I S T A I H D A K N G V L P
```
CCAAACCTCTCGAGCTAGTGGATGCCAGTGGTGCCAAGTGGATAGTGTTGAGAGTGGATG
```
K P L E L V D A S G A K W I V L R V D E
```
AAATCAAGCCTGATGTAGCACTCTTAAGGTAA
```
I K P D V A L L R *

PAP(1-262, N253D-Y254*) has a DNA (SEQ ID NO: 36) and amino acid sequence (SEQ ID NO: 37) of:

```
CTATGAAGTCGGGTCAAAGCATATACAGGCTATGCATTGTTAGAAACATTGATGCCTCTG
ATCCCGATAAACAATACAAATTAGACAATAAGATGACATACAAGTACCTAAACTGTGTATGG
GGGAGTGAAACCTCAGCTGCTAAAAAAACGTTGTAAGAAAAAAAGAAAGTTGTGAGTTAACT
ACAGGGCGAAAGTATTGGAACTAGCTAGTAGGAAGGGAAGATGAAGTCGATGCTTG
```
M K S M L V
```
TGGTGACAATATCAATATGGCTCATTCTTGCACCAACTTCAACTTGGGCTGTGAATACAA
```
V T I S I W L I L A P T S T W A V N T I
```
TCATCTACAATGTTGGAAGTACCACCATTAGCAAATACGCCACTTTTCTGAATGATCTTC
```
I Y N V G S T T I S K Y A T F L N D L R
```
GTAATGAAGCGAAAGATCCAAGTTTAAAATGCTATGGAATACCAATGCTGCCCAATACAA
```
N E A K D P S L K C Y G I P M L P N T N
```
ATACAAATCCAAAGTACGTGTTGGTTGAGCTCCAAGGTTCAAATAAAAAAACCATCACAC
```
T N P K Y V L V E L Q G S N K K T I T L
```
TAATGCTGAGACGAAACAATTTGTATGTGATGGGTTATTCTGATCCCTTTGAAACCAATA
```
M L R R N N L Y V M G Y S D P F E T N K
```
AATGTCGTTACCATATCTTTAATGATATCTCAGGTACTGAACGCCAAGATGTAGAGACTA
```
C R Y H I F N D I S G T E R Q D V E T T
```
CTCTTTGCCCAAATGCCAATTCTCGTGTTAGTAAAAACATAAACTTTGATAGTCGATATC
```
L C P N A N S R V S K N I N F D S R Y P

-continued

```
CAACATTGGAATCAAAAGCGGGAGTAAAATCAAGAAGTCAGGTCCAACTGGGAATTCAAA

T L E S K A G V K S R S Q V Q L G I Q I

TACTCGACAGTAATATTGGAAAGATTTCTGGAGTGATGTCATTCACTGAGAAAACCGAAG

L D S N I G K I S G V M S F T E K T E A

CCGAATTCCTATTGGTAGCCATACAAATGGTATCAGAGGCAGCAAGATTCAAGTACATAG

E F L L V A I Q M V S E A A R F K Y I E

AGAATCAGGTGAAAACTAATTTTAACAGAGCATTCAACCCTAATCCCAAAGTACTTAATT

N Q V K T N F N R A F N P N P K V L N L

TGCAAGAGACATGGGGTAAGATTTCAACAGCAATTCATGATGCCAAGAATGGAGTTTTAC

Q E T W G K I S T A I H D A K N G V L P

CCAAACCTCTCGAGCTAGTGGATGCCAGTGGTGCCAAGTGGATAGTGTTGAGAGTGGATG

K P L E L V D A S G A K W I V L R V D E

AAATCAAGCCTGATGTAGCACTCTTAGATTAA

I K P D V A L L D *
```

Another nucleic acid (SEQ ID NO: 38) encoding PAP(1-262, N253D-Y254*) (SEQ ID NO: 37) has the following sequence:

```
CTATGAAGTCGGGTCAAAGCATATACAGGCTATGCATTGTTAGAAACATTGATGCCTCTG

ATCCCGATAAACAATACAAATTAGACAATAAGATGACATACAAGTACCTAAACTGTGTAT

GGGGGAGTGAAACCTCAGCTGCTAAAAAAACGTTGTAAGAAAAAAGAAAGTTGTGAGTT

AACTACAGGGCGAAAGTATTGGAACTAGCTAGTAGGAAGGGAAGATGAAGTCGATGCTTG

M K S M L V

TGGTGACAATATCAATATGGCTCATTCTTGCACCAACTTCAACTTGGGCTGTGAATACAA

V T I S I W L I L A P T S T W A V N T I

TCATCTACAATGTTGGAAGTACCACCATTAGCAAATACGCCACTTTTCTGAATGATCTTC

I Y N V G S T T I S K Y A T F L N D L R

GTAATGAAGCGAAAGATCCAAGTTTAAAATGCTATGGAATACCAATGCTGCCCAATACAA

N E A K D P S L K C Y G I P M L P N T N

ATACAAATCCAAAGTACGTGTTGGTTGAGCTCCAAGGTTCAAATAAAAAAACCATCACAC

T N P K Y V L V E L Q G S N K K T I T L

TAATGCTGAGACGAAACAATTTGTATGTGATGGGTTATTCTGATCCCTTTGAAACCAATA

M L R R N N L Y V M G Y S D P F E T N K

AATGTCGTTACCATATCTTTAATGATATCTCAGGTACTGAACGCCAAGATGTAGAGACTA

C R Y H I F N D I S G T E R Q D V E T T

CTCTTTGCCCAAATGCCAATTCTCGTGTTAGTAAAAACATAAACTTTGATAGTCGATATC

L C P N A N S R V S K N I N F D S R Y P

CAACATTGGAATCAAAAGCGGGAGTAAAATCAAGAAGTCAGGTCCAACTGGGAATTCAA

T L E S K A G V K S R S Q V Q L G I Q I

TACTCGACAGTAATATTGGAAAGATTTCTGGAGTGATGTCATTCACTGAGAAAACCGAAG

L D S N I G K I S G V M S F T E K T E A
```

```
CCGAATTCCTATTGGTAGCCATACAAATGGTATCAGAGGCAGCAAGATTCAAGTACATAG

E  F  L  L  V  A  I  Q  M  V  S  E  A  A  R  F  K  Y  I  E

AGAATCAGGTGAAAACTAATTTTAACAGAGCATTCAACCCTAATCCCAAAGTACTTAATT

N  Q  V  K  T  N  F  N  R  A  F  N  P  N  P  K  V  L  N  L

TGCAAGAGACATGGGGTAAGATTTCAACAGCAATTCATGATGCCAAGAATGGAGTTTTAC

Q  E  T  W  G  K  I  S  T  A  I  H  D  A  K  N  G  V  L  P

CCAAACCTCTCGAGCTAGTGGATGCCAGTGGTGCCAAGTGGATAGTGTTGAGAGTGGATG

K  P  L  E  L  V  D  A  S  G  A  K  W  I  V  L  R  V  D  E

AAATCAAGCCTGATGTAGCACTCTTAGACTAA

I  K  P  D  V  A  L  L  D  *
```

Other non-cytotoxic PAP mutants that may be useful in the methods of the present invention are disclosed in Tumer, et. al. Nucleic Acids Research, 32:14 (2004) (see table therein), e.g., PAP(1-262, Y16M), PAP(1-262, T18M), PAP(1-262, M74R), PAP(1-262, W237*), PAP(1-262, L240*), PAP(1-262, R241*), PAP(1-262, V242*), PAP(1-262, E244*), PAP (1-262, A250*), PAP(1-262, L251*), and PAP(1-262, L252*). Yet other non-cytotoxic PAP mutants and methods of making thereof are disclosed in U.S. Pat. No. 6,627,736 and United States Patent Application Publication 2004/0241673, which are both herein incorporated herein by reference.

Other non-cytotoxic PAP mutants for use with the methods of the present invention may be determined by the protocol disclosed in example 1.

However, there are some non-cytotoxic PAP mutants that were found not to inhibit HCV replication such as PAP(1-262, Y72A) PAP(1-262, Y76A), and PAP(1-262, Y1231).

The PAP mutants described herein may be formulated into various dosage forms (depending upon the particular mode of administration) and in various dosage amounts for treating HCV in a human e.g., a human suspected of or diagnosed as having HCV infection, or for inhibiting translation of HCV RNA. Pharmaceutical compositions are typically prepared by admixing the PAP mutant with a pharmaceutically acceptable carrier. Carriers useful for purposes of the present invention include water, ethanol, polyols (e.g., glycerol, propylene glycol, and liquid polyethylene glycols), vegetable oils, nontoxic glycerol esters, lipids (dimyristoyl phosphatidyl choline), and mixtures thereof.

The PAP mutants are typically administered intravenously. Other parenteral modes of administration may include intramuscular and subcutaneous injection. Oral (solutions, syrups, emulsions, tablets, capsules, and the like) and other modes of administration may be useful as well.

In some embodiments, PAP mutant is administered in the form of a conjugate, wherein it is bound (e.g. covalently) to a ligand which specifically binds a receptor present on HCV infected cells, preferably liver cells. Thus, yet another aspect of the present invention is directed to a composition of matter comprising a non-cytotoxic PAP mutant that binds HCV IRES and inhibits translation of HCV RNA, conjugated (e.g., covalently bound) to a ligand, preferably a hepatocyte receptor-specific ligand. To target hepatocytes, proteins and polypeptides containing galactose-terminal carbohydrates, such as carbohydrate trees obtained from natural glycoproteins, can be used. For example, natural glycoproteins that either contain terminal galactose residues or can be enzymatically treated to expose terminal galactose residues (e.g., by chemical or enzymatic desialylation) can be used. In some embodiments, the hepatocyte receptor-specific ligand is an asialoglycoprotein, such as asialoorosomucoid, asialofetuin or desialylated vesicular stomatitis virus. Thus, conjugates of the present invention include, for example, PAP(1-262, PAP (1-262, N70A)-asialoglycoprotein, L71R)-asialoglycoprotein, asialoglycoprotein, PAP(1-262, Y123A)-asialoglycoprotein and PAP(1-262, E176V)-asialoglycoprotein.

Alternatively, suitable ligands for targeting hepatocytes can be prepared by chemically coupling galactose-terminal carbohydrates (e.g., galactose, mannose, lactose, arabinogalactan etc.) to nongalactose-bearing proteins or polypeptides (e.g., polycations) by, for example, reductive lactosamination. Methods of forming a broad variety of other synthetic glycoproteins having exposed terminal galactose residues, all of which can be used to target hepatocytes, are described, for example, Chen, et. al., Human Gene Therapy 5:429-435 (1994); and Ferkol, et al., FASEB 7:1081-1091 (1993) (galactosylation of polycationic histones and albumins using EDC); Perales, et al., PNAS 91:4086-4090 (1994) and Midoux, et al., Nucleic Acids Research 21(4):871-878 (1993) (lactosylation and galactosylation of polylysine using α-D-galactopyranosyl phenylisothiocyanate and 4-isothiocyanatophenyl β-D-lactoside); Martinez-Fong, Hepatology 20(6):1602-1608 (1994) (lactosylation of polylysine using sodiumcyanoborohydride and preparation of asialofetuin-polylysine conjugates using SPDP); and Plank, et al., Bioconjugate Chem. 3:533-539 (1992) (reductive coupling of four terminal galactose residues to a synthetic carrier peptide, followed by linking the carrier to polylysine using SPDP). See U.S. Pat. Nos. 6,069,133 and 5,985,655.

For example, in some other embodiments of the present invention, the PAP mutant is conjugated (e.g., by a disulfide bond) to a B chain of a type II RIP. Type II RIPs that may be used are ricin and Shiga-like toxin. Grandis, et al., J. Bacteriology 169:4313-4319 (1987), Jackson, et al., FEMS Microbiology Letters 44:109-114 (1987), Lamb, et al., Eur. J. Biochem. 148:265-270 (1985). Ricin conjugates bind galactose or N-acetylgalactosamine receptors on the surface of target cells and promote subsequent endocytosis of the PAP mutant. Conjugates containing the B chain of Shiga-like toxin or 2 bind the Gb3 receptor. Thus, by way of examples, conjugates of the present invention also include PAP(1-262, N70A)-ricin B, PAP(1-262, L71R)-ricin B, PAP(1-262, V73E)-ricin B, PAP(1-262, G75D)-ricin B, PAP(1-262, Y123A)-ricin B, PAP(1-262, E176V)-ricin B, PAP(1-262, N70A)-Shiga-like B-subunit, PAP(1-262, L71R)-Shiga-like B-subunit, PAP(1-262, V73E)-Shiga-like B-subunit, PAP(1-262, G75D)-Shigalike B-subunit, PAP(1-262, Y123A)-Shiga-like B-subunit and PAP(1-262, E176V)-Shiga-like B-subunit. Other ligand/hepatocyte receptor binding pairs useful for practicing the present invention will be recognized by those skilled in the art.

An amount of the PAP mutant is effective to inhibit translation of HCV RNA, which in turn inhibits or prevents propagation of HCV. The dosages (e.g. frequency and amount) of PAP mutant may vary, in accordance with various factors such as the severity of the disease, the overall health of the patient, body weight, age, etc. However, the dose should be sufficient to inhibit a substantial portion, e.g., up to 90% or more, of the virus replication in infected cells (e.g., of the patient). For example, in embodiments wherein the PAP mutant is administered in the form of a conjugate, the amount of the conjugate that would inhibit HCV replication by >90% if used at 10-100 μM range, is equal to about 2.0-20 ng/ml. The dose required to achieve this concentration can be calculated using the formula: Dose in micrograms=70×2(20)×wt (in kg)/1,000. For a 70 kg patient, this would yield a dosage of 10-100 micrograms. Dosages for adult humans with HCV infection envisioned by the present invention and considered to be therapeutically effective will generally range from between about 10 and 100 micrograms and will be administered with a frequency based on the plasma half life of PAP mutant in a given patient, as determined by solid phase ELISA. Higher doses can be employed in some cases, and the doses can readily be adjusted to provide appropriate amounts of the PAP mutant to children using the above formula.

EXAMPLES

Example 1

Inhibition of Translation of HCV RNA

Figure 2:
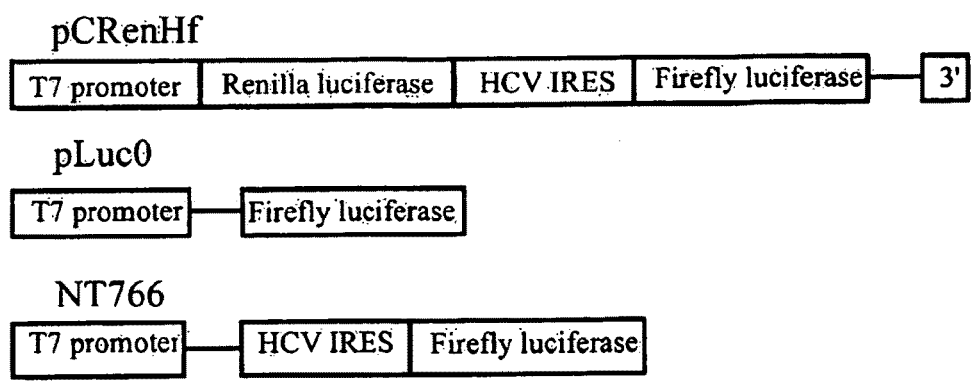
FIG. 2 is a schematic diagram showing the luciferase reporter constructs used in the translation experiments.

To examine the effect of PAP mutants on the HCV IRES directed translation, three constructs were used in the rabbit reticulocyte lysate in vitro translation system. The three constructs discussed herein (pCRenHF, pLucO, and NT766) are shown in FIG. 2. Construct pCRenHf contains the firefly luciferase (Fluc) gene under the HCV IRES downstream of the *renilla* luciferase (Rluc) under the T7 promoter. The second construct is the monocistronic NT766 in which the HCV IRES/Fluc cassette is under the control of the T7 promoter. The third construct is pLucO, in which Fluc is directly under the T7 promoter. The uncapped in vitro transcripts of these three constructs were produced by T7 RNA polymerase.

Wild-type PAP and the following six mutants were chosen to test their effect on the inhibition of HCV IRES directed translation: PAP(1-262, N70A) and PAP(1-262, V73E) that depurinate ribosomes, do not inhibit translation but destabilize mRNA; PAP(1-262, L71R) that depurinates ribosomes, inhibits translation, but does not destabilize mRNA; PAP(1-262, Y123A) that depurinates ribosome slightly, does not inhibit translation and does not destabilize its mRNA; PAP(1-262, G75D) and PAP(1-262, E176V) that do not depurinate ribosomes, do not inhibit translation and do not destabilize mRNA.

Figure 4:
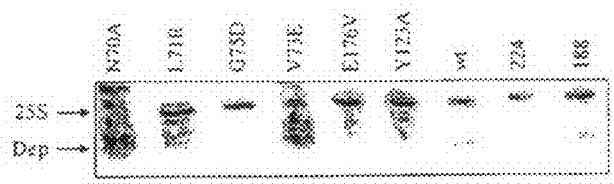
FIG. 4 is picture of PAP depurination of rRNA by primer extension analysis.

Wild type PAP and mutant proteins were isolated from bacterial cells with the H is Select cartridges (Sigma) after being induced for 4 hours by IPTG. Their rRNA depurination activity was assayed by primer extension analysis (FIG. 4). The results confirmed that PAP(1-262, N70A), PAP(1-262, L71R), PAP(1-262, V73E) and wild type PAP isolated from *E. coli* are able to depurinate ribosomes.

To examine their effect on translation in vitro, 1 μg transcript and 5 ng wt PAP or PAP mutants isolated from bacteria were added to the rabbit reticulocyte lysate in vitro translation mix at the start of the reaction. After 1 hr of translation, Fluc activity was measured using the Luciferase Reporter Assay System (Promega) in a Luminometer.

As shown in Table 2, wild-type PAP resulted in more than 90% reduction in the Fluc activity of all three transcripts. The PAP(1-262, N70A) inhibited these three transcripts by approximately 60% followed by PAP(1-262, L71R) with 25.4-29.3% of HCV IRES directed translation. The PAP(1-262, V73E) displayed 18.7-22.8% inhibition of the HCV IRES directed translation. The destabilizing and depurinating wild-type PAP, PAP(1-262, N70A) and PAP(1-262, V73E) inhibited translation of all three transcripts, while PAP(1-262, G75D) inhibited HCV IRES directed translation from the dual reporter, pCRenHf, but not translation from the single reporter constructs. The PAP(1-262, Y123A) did not inhibit translation. Similarly, the active site mutant, PAP(1-262, E176V) showed a very low level of translation inhibition. The PAP(1-262, N70A), PAP(1-262, L71R) and PAP(1-262, G75D) showed the strongest inhibition of HCV IRES directed translation, while PAP(1-262, V73E) showed a slightly lower level of inhibition. The PAP(1-262, N70A), PAP(1-262, L71R), PAP(1-262, G75D) and PAP(1-262, V73E) showed the strongest inhibition of HCV IRES directed translation.

TABLE 2

Percentage of in vitro translation inhibition of firefly luciferase in pCRenHf, NT766 and pLuc0 by PAP and mutants

| PAP | pCRenHf | NT766 | pLuc0 |
|---|---|---|---|
| wt | 92 ± 0.8 | 91.4 ± 1.2 | 91.7 ± 1.2 |
| N70A | 57.9 ± 2.7 | 56.3 ± 2.5 | 62.4 ± 2.1 |
| L71R | 29.3 ± 2.0 | 25.4 ± 1.6 | 36.7 ± 2.9 |
| V73E | 22.8 ± 1.9 | 18.7 ± 2.6 | 14.1 ± 2.9 |
| G75D | 27.2 ± 1.6 | 1 ± 1.4 | 4.7 ± 0.5 |
| Y123A | 1.7 ± 1.2 | 1.4 ± 1.9 | 0.4 ± 0.5 |
| E176V | 15.6 ± 2.3 | 22.4 ± 2.6 | 40.3 ± 2.8 |

Results are also summarized in FIG. 3.

Example 2

Binding of PAP Mutants to HCV IRES

The Biacore 3000 SPR (surface plasmon resonance)-based biosensor system was employed to study the binding of PAP and mutants to SRL and HCV SLII and SLIIId. Three oligoribonucleotides were synthesized by IDT Inc. (Coralville, Iowa): SRL 27-mer (5'-CCUGCUCAGUACUAGAGGAAC-CGCAGG-3' (SEQ ID NO: 39)) for the sarcin ricin loop of rRNA, SLII 38-mer (5'-CACGCAGAAAGCGUCUAGC-CAUGGCGUUAGUAUGAGUG-3' (SEQ ID NO: 40)) for the HCV SLII, SLIIId 27-mer (5'-GCCGAGUAGUG-UUGGGUCGCGAAAGGC-3'(SEQ ID NO: 41)) for the HCV SLIIId. The oligos were 5'-end-biotinylated and HPLC-purified.

The binding of PAP and mutants was also tested on mutated SLII and SLIIId. The mutant A96d is an HCV IRES with the A96 (adenosine #96) removed from the SLII loop. The mutant A260d is an HCV IRES with A260 (adenosine #260) removed from the SLIIId loop. The A96 in SLII and A260 in SLIIId are the equivalent of nucleotides A4321 in SRL of 28S rRNA that can be depurinated by PAP. The oligoribonucleotides synthesized by IDT Inc. (Coralville, Iowa) for experimentation on mutated SLII (A96d) and SLIII (A260d) respectively are as follows: SLII 37-mer with A96 deleted (SLII A96d, 5'-CACGCAGAAAGCGUCUAGC-CAUGGCGUUAGUUGAGUG-3' (SEQ ID NO: 42)) and SLIIId 27-mer with A260 deleted (SLIIId A260d, 5'-GC-CGAGUGUGUUGGGUCGCGAAAGGC-3' (SEQ ID NO: 43)).

Without being bound by any particular theory of operation, if PAP acts by binding and depurinating A96 of SLII and/or A260 of SLIIId, the binding of PAP to SLII and SLIIId will be reduced when A96 and/or A260 are deleted.

The protocol for Biacore analysis using the Biacore 3000 instrument was as follows. The oligo (40 μg/ml) was immobilized on the surface of the streptavidin (SA) sensor chips by injecting 30 μl of the oligo at a flow rate of 5 μl/min in HBS-EP buffer (0.1 M HEPES, pH 7.4, 0.15 M NaCl, 3 mM EDTA, and 0.005% polysorbate 20). The unoccupied SA surface was blocked by injecting 30 μl of 25 μg/ml biotin in HBS-EP at a flow rate of 5 μl/min. PAP and mutant proteins purified from bacteria were prepared in HSEM buffer (10 mM HEPES, pH 8.0, 50 mM NaCl, 1 mM EDTA, 5 mM $MgCl_2$) to yield a final concentration of 5 μg/ml.

In a kinetic study, 30-μl samples (750, 375, 187, 93 nM) were injected sequentially at 25° C. at a flow rate of 8 μl/min onto the sensor chip surface, using HBS-EP as the running buffer. Between samples, the binding surfaces were regenerated by a 3-min injection of 2 M NaCl at a flow rate of 10 μl/min.

To analyze the data, base lines were adjusted to zero for all curves, and the injection start times were aligned. Background sensorgrams were subtracted from the experimental sensorgrams to yield curves representing specific binding. The association and dissociation phases of the sensorgrams were fit simultaneously, assuming a simple bimolecular reaction model for interaction between soluble analyte and immobilized ligand, equivalent to the Langmuir isotherm for adsorption to a surface. The association and dissociation rate constants were calculated by nonlinear fitting of the primary sensorgram data using the BIAevaluation software (version 4.1), supplied with the instrument (Biacore Inc.). Affinities ($K_D$) were calculated from the rate constants and from analysis of equilibrium binding. Any $K_d$ with a value more than 1000 nM is considered to have no binding to the IRES elements and marked with "–" in table 3 below.

Figure 5:
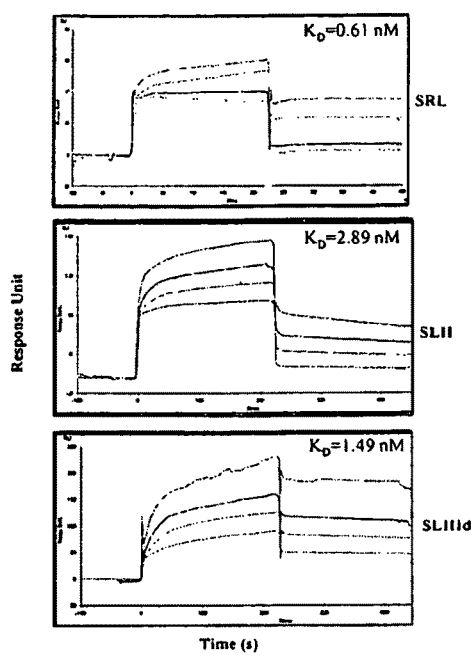
FIG. 5 is a graph showing binding affinity of wild-type PAP to SRL, HCV IRES SLII, and HCV IRES SLIIId measured by the Biacore 3000.

As shown in FIG. 5, wild-type PAP had different affinities for the SRL, SLII and SLIIId. It had the strongest affinity for the HCV SRL ($K_D$=0.61 nM). The binding affinity of wild-type PAP for SLIIId was 1.49 nM. The affinity ($K_D$=2.89 nM) of wild-type PAP for SLII is lower than SRL and SLIIId. These results suggested that binding of wild-type PAP to HCV SLIIId might be more significant for inhibition of HCV IRES-mediated translation than its binding to HCV SLII. Table shows that nontoxic PAP mutants have lower affinities for SRL than for HCV SLII and SLIIId. The PAP(1-262, N70A), PAP(1-262, L71R) and PAP(1-262, G75D) mutants showed stronger affinity for SLIIId than for SLII. These mutants had the most inhibitory effect on HCV IRES directed translation (Table 3), providing evidence that the binding of PAP and mutants to SLIIId may be more important than binding to SLII for inhibition of HCV IRES directed translation.

TABLE 3

Binding affinities ($K_D$) of wt PAP and mutants to SRL and HCV IRES SLII and SLIIId determined by Biacore 3000

| PAP | SRL $K_D$ (nM) | SLII $K_D$ (nM) | SLIIId $K_D$ (nM) | A96d $K_D$ (nM) | A260d $K_D$ (nM) |
|---|---|---|---|---|---|
| wt | 0.61 | 2.89 | 1.49 | 85.5 | 65.7 |
| N70A | 3.42 | 2.75 | 1.09 | 5.99 | 90.9 |
| L71R | 162 | 2.91 | 0.952 | 28.4 | — |
| V73E | — | 6.39 | 1.58 | 2.79 | 10 |
| G75D | — | 0.493 | 2.46 | 953 | 41.9 |
| Y123A | — | 1.66 | 7.94 | 45 | 10.4 |
| E176V | 1.17 | 2.65 | 30.3 | 434 | 33.4 |

Example 3

Ricin does not Bind HCV IRES

The Biacore 3000 SPR based biosensor system was employed to study the binding of Ricin to SRL, HCV SLII and SLIIId. Three oligoribonucleotides were synthesized by IDT Inc. (Coralville, Iowa): SRL 27-mer (5'-CCUGCU-CAGUACUAGAGGAACCGCAGG-3' (SEQ ID NO: 39)) for the sarcin ricin loop of rRNA, SLII 38-mer (5'-CACGCA-GAAAGCGUCUAGCCAUGGCGUUAGUAUGAGUG-3' (SEQ ID NO: 40)) for the HCV SLII, SLIIId 27-mer (5'-GCCGAGUAGUGUUGGGUCGCGAAAGGC-3' (SEQ ID NO: 41)) for the HCV SLIIId. The oligos were 5'-end-biotinylated and HPLC-purified.

The protocol for Biacore analysis using the Biacore 3000 instrument was as follows. The oligo (40 μg/ml) was immobilized on the surface of the streptavidin (SA) sensor chips by injecting 30 μl of the oligo at a flow rate of 5 μl/min in HBS-EP buffer (0.1 M HEPES, pH 7.4, 0.15 M NaCl, 3 mM EDTA, and 0.005% polysorbate 20). The unoccupied SA surface was blocked by injecting 30 μl of 25 μg/ml biotin in HBS-EP at a flow rate of 5 μl/min. PAP and mutant proteins purified from bacteria were prepared in HSEM buffer (10 mM HEPES, pH 8.0, 50 mM NaCl, 1 mM EDTA, 5 mM $MgCl_2$) to yield a final concentration of 5 μg/ml.

In a kinetic study, 30-μl samples (750, 375, 187, 93 nM) were injected sequentially at 25° C. at a flow rate of 8 μl/min onto the sensor chip surface, using HBS-EP as the running buffer. Between samples, the binding surfaces were regenerated by a 3-min injection of 2 M NaCl at a flow rate of 10 μl/min.

To analyze the data, base lines were adjusted to zero for all curves, and the injection start times were aligned. Background sensorgrams were subtracted from the experimental sensorgrams to yield curves representing specific binding. The association and dissociation phases of the sensorgrams were fit simultaneously, assuming a simple bimolecular reaction model for interaction between soluble analyte and immobilized ligand, equivalent to the Langmuir isotherm for adsorption to a surface. The association and dissociation rate constants were calculated by nonlinear fitting of the primary sensorgram data using the BIAevaluation software (version 4.1), supplied with the instrument (Biacore Inc.). Affinities ($K_D$) were calculated from the rate constants and from analysis of equilibrium binding.

As shown in table 4, Ricin has a low affinity for SRL, SLII and SLIIId.

TABLE 4

Binding affinities ($K_D$) of Ricin to SRL and HCV
IRES SLII and SLIIId determined by Biacore 3000

| RTA | SRL $K_D$ (nM) | SLII $K_D$ (nM) | SLIIId $K_D$ (nM) |
|---|---|---|---|
| RTA | 10800 | 1000 | 183 |

Example 4

Preparation of Recombinant PAP and Mutants

Yeast cells *Saccharomyces cerevisiae* were transformed with NT188 (wild-type PAP), and the non-toxic mutants, PAP(1-262, E176V) (the active site mutant), PAP(1-262, N70A), PAP(1-262, L71R), PAP(1-262, G75D), PAP(1-262, V73E) and PAP(1-262, Y123A). Six hours after induction, the cells were harvested by centrifugation and washed three times with 10 ml ice-cold WCE-Mannitol buffer, which consists of 30 mM HEPES, pH7.4, 100 mM KAc, 2 mM MgAc, 2 mM DTT and 8.5% Mannitol. They were then resuspended in WCE-PMSF-Mannitol buffer, which consists of WCE-Mannitol with 0.5 mM phenylmethylsulfonyl fluoride (PMSF). The cells were lysed and cell debris was removed by centrifugation at 6.5 K rpm for 10 minutes. The cleared lysate was centrifuged at 14 K rpm for 10 minutes to remove lipids and the insoluble material. The lysate was then centrifuged again at 100 K rpm for 30 minutes to remove ribosome contamination. The lysate, containing the PAP proteins was filtered through Sephadex G-25 column equilibrated with WCE-PMSF buffer to remove any translation inhibitors. Iizuka, et al., Methods 11:353-60 (1997).

Example 5

Inhibition of HCV IRES Translation in Hep G2 Cells

Hep G2 cells, obtained from ATCC, were used as a model to show inhibition of HCV IRES translation. Hep G2 cells are human hepatocellular carcinoma cells. Plasmid pCRenHf containing the cap-dependent *Renilla* luciferase gene and the HCV IRES-dependent firefly luciferase gene was transfected into Hep G2 cells together with either wild-type PAP or PAP mutants that have been cloned into a mammalian expression vector, pCAGGS (Invitrogen). The Hep G2 cells were maintained in eagles minimum essential medium (EMEM) supplemented with 10% fetal bovine serum. The Hep G2 cells were transferred to a 24-well plate and grown to 90% confluency. Lipofectamine™ (Invitrogen) was diluted in EMEM and mixed with plasmid DNA. Cells were transfected with 0.8 μg of plasmid DNA each sample with two replicates. The transfected Hep G2 cells were incubated at 37° C. in 5% $CO_2$ for 24 hr. Hep G2 Cells were harvested and lysed with passive lysis buffer in the Dual-Luciferase® Reporter Assay system (Promega). The activities of *Renilla* luciferase (Ren Luc) and firefly luciferase (FF Luc) were measured with a luminometer. Inhibition of luciferase activity by wild-type PAP and PAP mutants were calculated and compared to-cells transfected with only pCRenHf. The experiment was repeated three times and is summarized in FIGS. 7a and 7b.

Figure 7A:
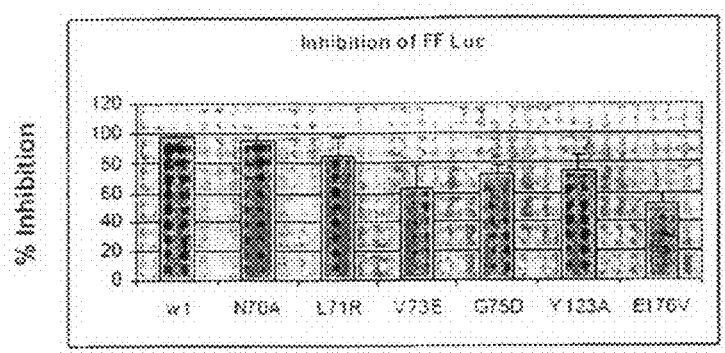
FIG. 7a is a graph showing inhibition of IRES-dependent FF Luc translation.
Figure 7B:
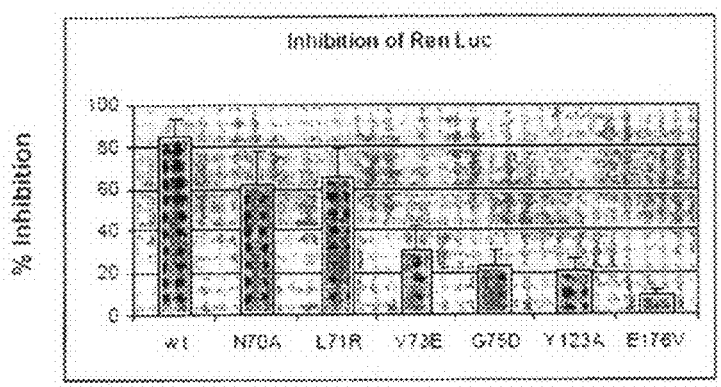
FIG. 7b is a graph showing inhibition of cap-dependent Ren Luc translation.

The results in FIG. 7a showed that wt PAP, PAP(1-262, N70A) and PAP(1-262, L71R) inhibited the IRES-dependent FF Luc translation by 80-99% followed by PAP(1-262, V73E), PAP(1-262, G75D), PAP(1-262, Y123A) and PAP(1-262, E167V) with 50-70% inhibition. The results in FIG. 7b showed the inhibition of PAP, PAP(1-262, N70A) and PAP (1-262, L71R) to the cap-dependent translation of Ren Luc. Inhibition was determined to be 70 to 90% while PAP(1-262, V73E), PAP(1-262, G75D), PAP(1-262, Y123A) and PAP(1-262, E167V) only inhibited 10-30% of Ren Luc. This indicates that the non-toxic, non-depurinating PAP(1-262, G75D), PAP(1-262, E167V) bind to the IRES SLII and SLIIId and inhibit IRES-dependent translation without significantly affecting the cap-dependent translation. The non-toxic, less-depurinating PAP(1-262, Y123A) can also bind to SLII and SLIIId well and inhibit the IRES-dependent translation without greatly affecting the cap-dependent translation.

INDUSTRIAL APPLICABILITY

The present invention has applicability in clinical medicine and for the treatment of HCV infection.

All patent and non-patent publications cited in this specification are indicative of the level of skill of those skilled in the art to which this invention pertains. All these publications are herein incorporated by reference to the same extent as if each individual publication or patent application were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A composition of matter comprising a non-cytotoxic PAP mutant that binds HCV IRES and inhibits translation of HCV RNA, conjugated to a hepatocyte receptor specific ligand wherein said mutant is SEQ ID NO: 1 having at least one amino acid substitution selected from the group consisting of N70A, L71R, V73E, G75D, Y123A, E176V, and said hepatocyte specific ligand is selected from the group consisting of ricin B, Shiga-like B subunit and asialoglycoprotein.

2. The composition of claim 1, wherein said ligand is ricin B.

3. The composition of claim 1, wherein said ligand is Shiga-like B-subunit.

4. The composition of claim 1, wherein said ligand is asialoglycoprotein.

5. The composition of 1, wherein the PAP mutant has a N70A amino acid substitution.

6. The composition of claim 1, wherein the PAP mutant has a L71R amino acid substitution.

7. The composition of claim 1, wherein the PAP mutant has a V73E amino acid substitution.

8. The composition of claim 1, wherein the PAP mutant has a G75D amino acid substitution.

9. The composition of claim 1, wherein the PAP mutant has a Y123A amino acid substitution.

10. The composition of claim 1, wherein the PAP mutant has a E176V amino acid substitution.

* * * * *